(12) United States Patent
Tai et al.

(10) Patent No.: US 10,186,332 B2
(45) Date of Patent: Jan. 22, 2019

(54) DETERMINATION DEVICE, COMPUTER READABLE MEDIUM, AND MARKER FOR OBTAINING INFORMATION ON LUNG CANCER

(71) Applicants: SYSMEX CORPORATION, Kobe-shi, Hyogo (JP); THE UNIVERSITY OF TOKYO, Tokyo (JP)

(72) Inventors: Kaya Tai, Kobe (JP); Genta Nagae, Tokyo (JP); Hiroyuki Aburatani, Tokyo (JP)

(73) Assignees: SYSMEX CORPORATION, Kobe-shi, Hyogo (JP); THE UNIVERSITY OF TOKYO, Bunkyo-ku, Tokyo (JP)

( * ) Notice: Subject to any disclaimer, the term of this patent is extended or adjusted under 35 U.S.C. 154(b) by 593 days.

(21) Appl. No.: 14/795,089

(22) Filed: Jul. 9, 2015

(65) Prior Publication Data

US 2016/0012201 A1    Jan. 14, 2016

(30) Foreign Application Priority Data

Jul. 10, 2014  (JP) .................. 2014-142494

(51) Int. Cl.
  *G16H 50/30*    (2018.01)
  *G06F 19/00*    (2018.01)
  (Continued)

(52) U.S. Cl.
  CPC ........... *G16H 50/30* (2018.01); *C12Q 1/6886* (2013.01); *G06F 19/00* (2013.01); *G06F 19/22* (2013.01); *C12Q 2600/154* (2013.01)

(58) Field of Classification Search
  None
  See application file for complete search history.

(56) References Cited

U.S. PATENT DOCUMENTS

| 2012/0202202 A1 | 8/2012 | Wang et al. |
| 2014/0031257 A1* | 1/2014 | Lothe ............... C12Q 1/6886 506/9 |
| 2014/0356866 A1* | 12/2014 | Sakai .................. C12Q 1/68 435/6.11 |

FOREIGN PATENT DOCUMENTS

| WO | 2007/008693 A2 | 1/2007 |
| WO | 2007/008693 A3 | 1/2007 |

(Continued)

OTHER PUBLICATIONS

Selamat et al. Genome-scale analysis of DNA methylation in lung adenocarcinoma and integration with mRNA expression. Genome Research. 2012, vol. 22, No. 7, p. 1197-1211.*

(Continued)

*Primary Examiner* — John S Brusca
*Assistant Examiner* — Olivia M Wise
(74) *Attorney, Agent, or Firm* — Sughrue Mion, PLLC

(57) ABSTRACT

A determination device for enabling a computer to carry out a process including the steps of: obtaining an analysis result on methylation status of a CpG site located in a promoter region of at least one gene selected from HOXB4 (Homeobox B4) and ZSCAN31 (zinc finger and SCAN domain containing 31) in a DNA sample derived from a subject; and outputting a determination result as information on lung cancer in the subject based on the resulting analysis result is provided. A computer readable medium and a marker for obtaining information on lung cancer are also provided.

10 Claims, 12 Drawing Sheets

Specification includes a Sequence Listing.

(51) Int. Cl.
    *G06F 19/22*    (2011.01)
    *C12Q 1/6886*   (2018.01)

(56) References Cited

FOREIGN PATENT DOCUMENTS

WO    2013/177265 A1   11/2013
WO    2013/177265 A8   11/2013

OTHER PUBLICATIONS

Tibor Rauch et al., "Homeobox gene methylation in lung cancer studied by genome-wide analysis with a microarray-based methylated CpG island recovery assay", PNAS, Mar. 27, 2007, pp. 5527-5532, vol. 104, No. 13.

Domenico Flagiello et al., "Relationship between DNA methylation and gene expression of the HOXB gene cluster in small cell lung cancers", FEBS Letters 380 (1996), pp. 103-107.

Steven H Lin et al., "Genes suppressed by DNA methylation in non-small cell lung cancer reveal the epigenetics of epithelial-mesenchymal transition", BMC Genomics 2014, 15:1079, pp. 1-15.

\* cited by examiner

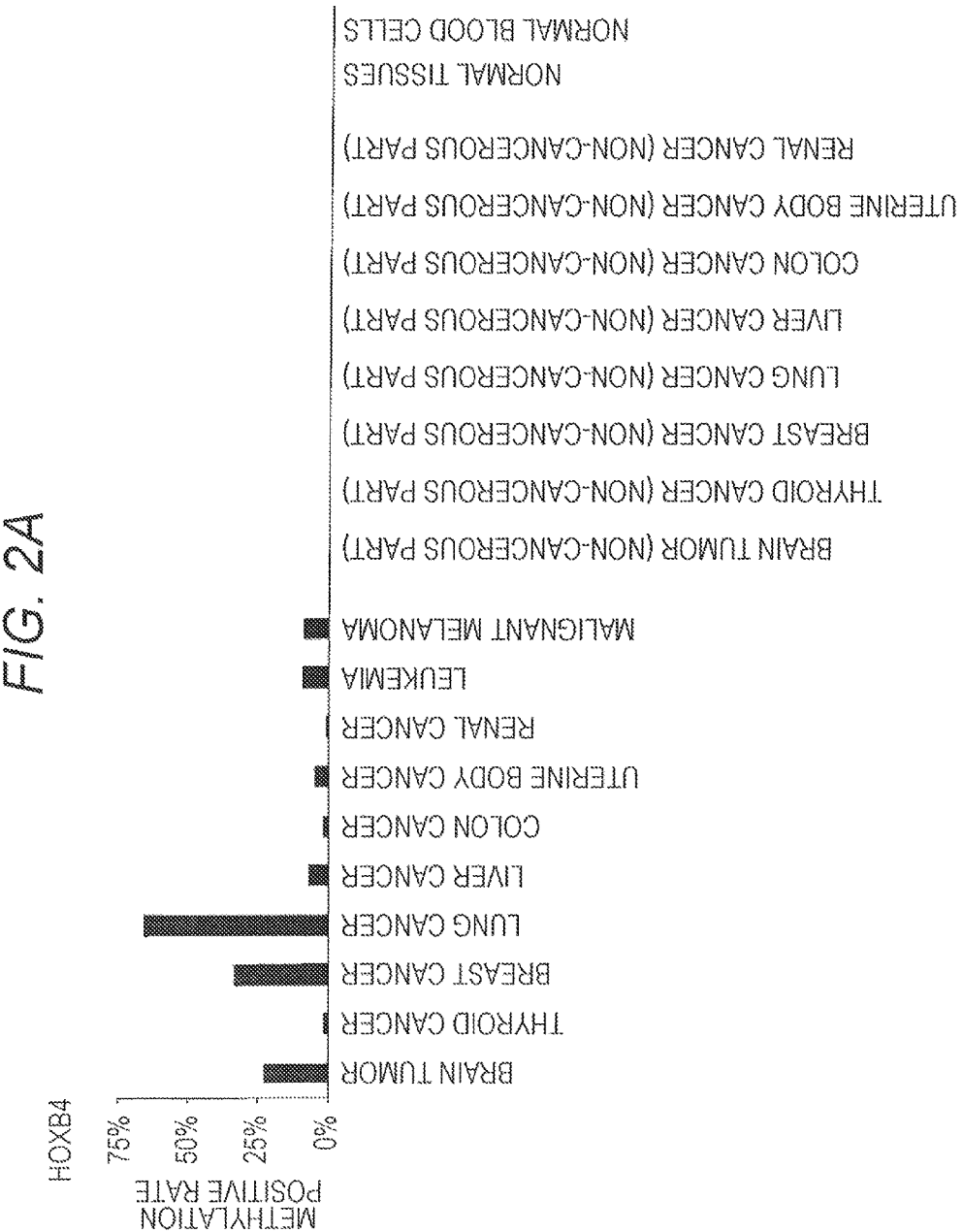

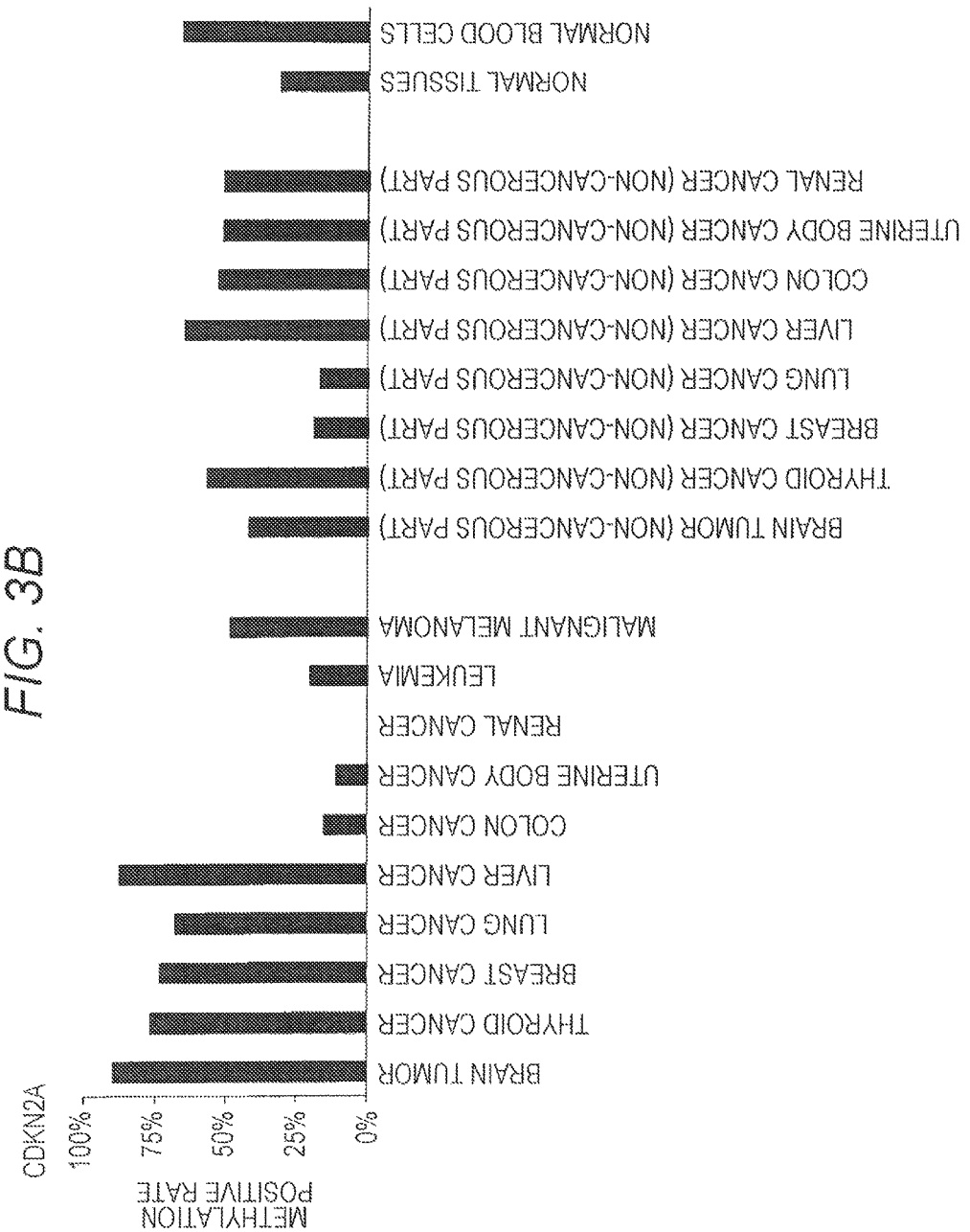

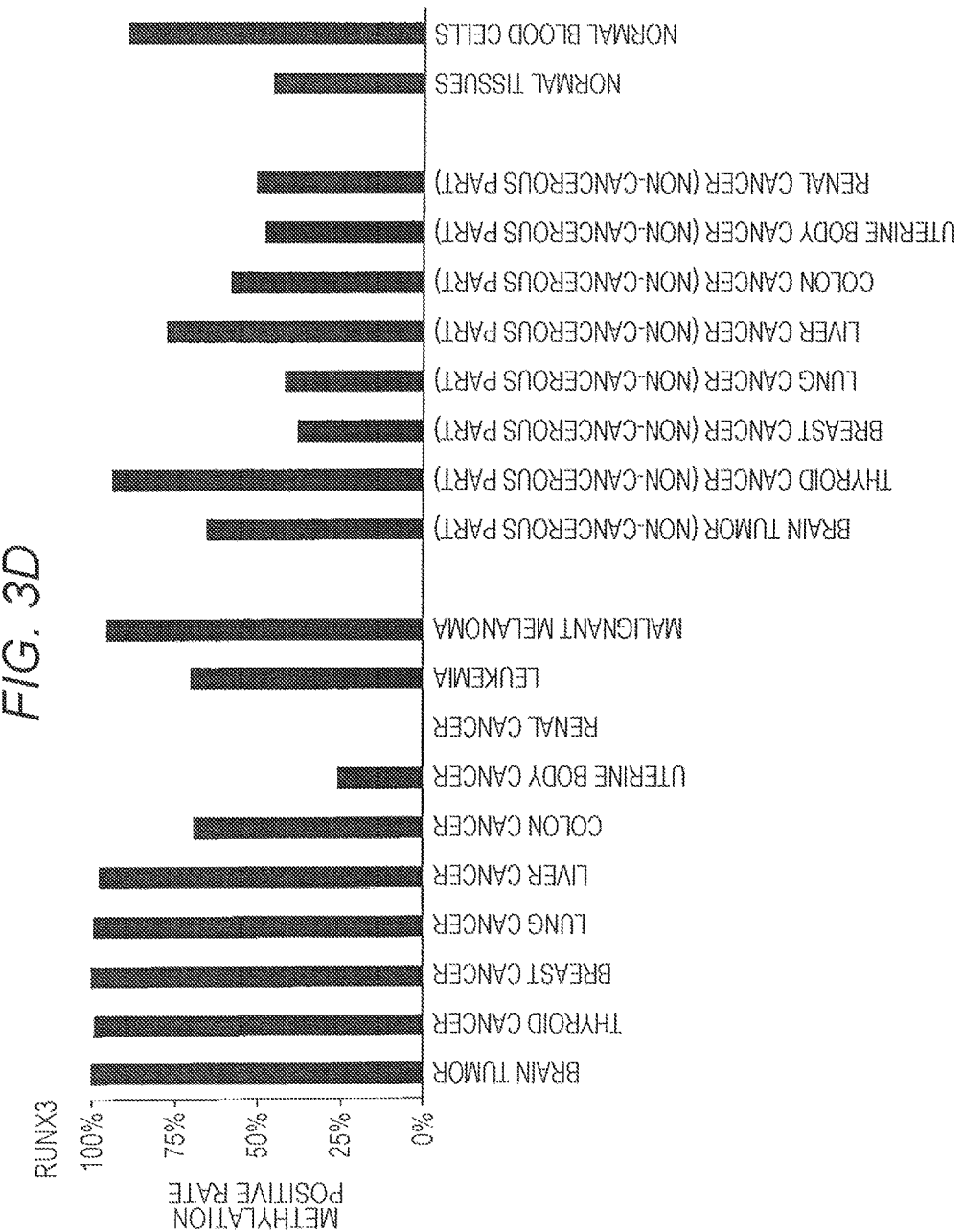

SEQUENCE LISTING

<160> NUMBER OF SEQ ID NOS: 12

<210> SEQ ID NO 1
<211> LENGTH: 4118
<212> TYPE: DNA
<213> ORGANISM: Homo sapiens

<400> SEQUENCE: 1

```
tctctttttc cttggactca attttcctgc tcactcctga gttgtcaagg ccacccctt      60 ccctacttgc tcccctcctc tgttgcccac ccccaacccc acgrtggaag tgggtgagca     120
gtcattctgg ccctcagtga atgggcacga aagatgaggg agagtgtgtg tgtgttaccg    180
tgaccaaaac actgcactat ctggcagtca gagggtgctt tcgctgggta tcgggagtgg    240
gggacaaaga aaggaaatcc aggctgtctt ccagcagcgg cagtagcaga ggcggaggcg    300
gccgagccgg gcctcatttg ttagcgggtg tcgaggtaat ggtcgccacc gaggcccgtc    360
ttctcctcgg cagaggaaac aagacagatg ggcctggacc tggcgtgatt aaagatgaaa    420
cgtggatcca tcttcgccaa agctgaaaac gaggagctgc agcctcctcc tatttctctt    480
tctgtctttt tctttcttcc ttcttcttgc ttttctttt tcttttttt aagaaagaaa     540 gcaagagatt tgaatcttgc ttctggggggg gcctcccgt ggccctctat tgtcatttct    600
ataaataaag cttcccctcc ccctcttctg cgtttattcg tatataagt gtgggggagg     660 gcagatagat ttttccgggg cccaggcccc agggcccct cctgtccccc caccccatcc     720
cctgcactca ctgcccaccc ccaccccgag gttcgtggct cccgcgtgcg ggggcactag    780
agcgcgcggg ggcctccatt gggccggcca ggggccctc cggctgagcc tgccgcacca    840
cccgagcgga tcttggtgtt gggcaacttg tggtcttttt tccacttcat gcgccggttc    900
tggaaccaga tcttgatctg gcgctcggag aggcagagcg cgtgggcgat ctccaccctc    960 cggcgccgt tcaggtagcg gttgtagtga aattccttct ccagctccaa gacctgctgg   1020
cgcgtgtagg cggtccgaga gcgcttgggc tccccgccgg cgtaattggg gtttactgga   1080
```

```
cacacacgga gagagggaga aagagaaagt tttattgccc ccgaaagaga gagtcctttc      1140
ttccagggaa cacagcgttt ccctccctcc ctctcccgcc acctcttctt ccttctgagg      1200
gagagcgggg aaaaacgaaa agggaagaat gcaagaccca agaatgagaa agagacctcc      1260
aagttttgga gggctgtgct gtgtcctttgt ttgggtgtgt ggtggggaag gggggcgtgt     1320
gaggactccc ccaaggtttt aattgctcct ctctccccct cagcttgggg ccccagaat      1380
gggagaatga gggggtggaa gagggagggg aggtttccct aaaccttttcc tctgtttagt    1440
tcccacccctt gctgctcaga ttccaagcag tgcctacccc tactgaaaac ttttgctcac   1500
ttctccagcc aaggagtcag actggaagaa aggaaaaaat aaatactggg agttgactca     1560
actctctgct taaatacgga ttacctcctc ctccttctcc tcctccacct cctccacccc     1620
tccccaactt ccaacttcat taagactgta tctccctggc gaaaaagtcg ctggtgagaa     1680
tggtgaagag gatggggaac ctacttcaaa ggcgcagggc ccaccaggcc ataaaaattt     1740
atggggatg taattatgtg gctctgaaaa caggcgaccg taaatctccg gcaatggcga      1800
gtttatagcg gggacaattg gcttccccag ctcaaccccc ccccaaccca tgcctccgaa     1860
gtcccttgg tgtaaagctc caggggtggg aggggaagg ggtgcccacg cactcacccg       1920
tgctcacgtg aactttgcgc atccaggggt agacgacggg ctcttgcac gcggagtggg      1980
acgggctggg gtgcagggg ttctgggcgc agggaggcgg cgggggctg ctgctgaccg       2040
cctcgcagcc ctggccgggc tccggagga gggcccggc gggtggcggc gcaggagccc       2100
gaggggacag accgggcggt ggcgggggcg gcggggtgg tggcggaggc ggcgggggcc      2160
cagggtcccg gcaggccgcg tagcgctgca cggtgcacgc cgcgcgccgc ccgaagcccg    2220
cctccggctg gaagctgctc tctcgcctct ggccgccggc gtagtacccg ggcgagtggt     2280
cgctgggtag gtaatcgctc tgtgaatatt cctcgcatgg agggaacttg gggtcgacat    2340
agtttgagtt gatcaaaaaa gaactcatag ccattaattt ctgggaattg cccacaaaat    2400
atactaaaat ttattccgac ccctgactcg ttttcctgtt tccgaaagcc ctcctactta    2460
ctgtcaagtg aacaaagtta ggcgcccacg tgatcctccg agccaatggc cgccccgcct    2520
gcgattcccg gataaggaaa tctgctcacc cggaccccac tccagccaaa gaggtttatt    2580
tccccttctt cccttcccc tccccacccca cccacccaac accaggattt acatagggct    2640
cctgcgggc gaccccctcc ttgcctcgct ctctccggga tcagagagag agcgagagag     2700
agagcgcgcg caggttgcga ctggagggcc tgttggggcg ctaggcagag cgcaaaccct    2760
agatcccctta agaagttggg gctcccggtg tagccctcct gttctgcctc acctctgccc    2820
agcattctgt accttccaaa ggccccagtc tcctcccctc ggcgggaggg agcgctagca    2880
ccctgcgtct ctatggggag ttaggttact ggcgggttgg gggctccgtc tcgaaagggg    2940
aacccatacg ggggccagag cacagagctt ggggcttttc tctgcagctg gatggggaag    3000
ggtaggggtg agagaggagg cgtccagagc tagaggcgg gtgcgcagag ggacttgtca    3060
gagatgaatg gaaccgcggg cggatcgata ggaaattcat gcactaattc ggggagactt    3120
cgccttccaa atctcattta gctgcacggt tagctagact gtgtccgtca gtccgtctgt    3180
cccccttctc ctatccactc ctcccttaa cccacacggc caagcctgg agaaacgact      3240
tggtttccca cactatagac agagcgctgg ggtaaaaaaa cctgcaactt ttgagagcaa   3300
aattgattag caatttgcta attccataac caccccgagca atactaacca tgggtccgag   3360
acgttctaat tgtcgccgcc tccgcggcga atagaaatct cacatccctt tgatactggg    3420
gatacagcca tagaggtgac ccacacagac aataacactc cttggtaatc gagtatttcc     3480
```

```
aggtcatctt gttctgaact gaaacggaaa ggcggcctca gcatccgttt gttaaacaaa    3540
tttcctttgc cttcttcgca cactgaagac aagtcatttt ttttcgcaat ttccaataaa    3600
gcctccctga gcccagaata gaaaatgggt gcgtttggga cgagaagata aatttaaaac    3660
ttcaacaaca ataacattaa cctcttaaag agatgtgaaa agggaccaag gctcccaggg    3720
gcaggcgtgg ggagagttca ggtagatgat ttctccatct ctaaccagtt gaaggaggaa    3780
aagatagagg aataaagagg aaggagtctt cgtgtggcca gtcaccagac tgtcctcatt    3840
cagaaaaata ctacatatac atatatatat atttttttct tctggaaaaa taagagcgga    3900
gtgtttatgt caactacata ttcccctaga tacgaatttg tgaccacaaa attccttaca    3960
caaattcgga tctacagggt atatacagaa gacagacaga tcttcttggc ccagaaattt    4020
tccagttctc ctactttccg cgccttcttc gtttggggtg tggtttgagt gctttggttt    4080
tatttcgttt tgttctagtt ttgagctctg ggaacaga                           4118

<210> SEQ ID NO 2
<211> LENGTH: 4121
<212> TYPE: DNA
<213> ORGANISM: Homo sapiens

<400> SEQUENCE: 2
cacatatatt tactaagtgt ttacgaggtg tcagacagca aagagtgaaa caatgcagaa      60
tttgatgtgt ccccactgtc cttcaccgaa ataaaaacat ggcagaaaga gcataaaaga     120
gaatgttttc attcatgaga atgttttcat tcacgtcagc ataattaaca acagcaacaa     180
agagatcatg taaatcacaa atcatgtgtg ttgtaaaata aatcccaaag gataccaatt     240
acgatgacaa gaaaacagaa gaagacctta aataccatga ggaaacagtc aaatccagaa     300
atggggatgc actacaggaa gactggaaga gcctcctttt aaacaaggca atgggatggg     360
aggaagggag gcaaagagta aaattgccct aggttaagac tcaactacat gcagtgagtg     420
gtctatgatt ggatcctagt tggtacaaac aggtataaaa gacatctgtg ggacaacagg     480
gggtggaagg atttaaacat gaactaggtg ttaggtgaag cgcctacact tagttgggtg     540
tgctaataat cttgtggtta tgtagggaaa tgtcccaatt tttagagat gcattagaaa      600 ctagaggtga caagttatga ggttggtggt ttttacaata tttaaagaaa acatatgcga     660
caaacattgc ataatgttga cttattaaat aaaaattacg tgtatatagg aaataaggct     720
tttgacaggg agagaccctt ctctacctct ggacctcggt ttcgccgcaa agctccgacc     780
tctctagggg tctctcccac caccctgtga aagggctacc tagcttgcct taggtggata     840
gcaagggaag ggtccctgga gagcctgccc ccgcccatga tttagtgtct tatccccaca     900
taacataaaa ctaagcctgg ggaaaaaatc aggttgcagg caccgataag ggaactagca     960
cagggtgttg tgcctagaga tatgcccacg gctgcataga tagaaaaacc tcgggcccat    1020
ttggataaaa acttgcacag aacctccagc tcactcagat aagggaacaa ggcctgacac    1080
ataatgcctt tgtcctttgt atagtcagca ggttcccagg aaaagtttct tctccttttg    1140
tgggtatgga cacggtgggt tctggtaggt tccggcaggc gctctacttt cctttattag    1200
gactataagc ccagcttctg tgaatcatca cctcagcccc tgattggtcc ggggccaaac    1260
tttcacttcg gcttctgata ggtcctgggc caagctaagc agcagctatg aatcatcatt    1320
tcagctcctg attggtcccg gaccaagctg agtcaagcgt cgccaggac agcccgcaga    1380 ctaagcgcat tccctctcct ttccagtcca taaaaccccc agaacgggcc ccataatggg    1440
```

```
tactcccggt cgggacccct tctctgctgg cagagagctt tttcctttcg cttattaaac    1500
tttcgctcta acctcacctt tgtgtctgcg ctcctttatc gtcttggagg caggacaaag    1560
aactccgggc gttatctcag acaaagaaag gctgtttaat cttcaggata aggggcggga    1620
cctccaccta ctccacgggg gcttcaggcc agtgaatgtg tagggcgggg gtcacgcct    1680 gcgcagacgt tccctccccg cctactccaa ggcacagacc tgaaatcttc tgggaacctg    1740
gcgggtcgcg acaaggggcc aagactcacc ttcggggcac cggcaagcta cggaacaggt    1800
ggcggggctg cagcacccca atgaccgatc aaccgcaaag gccggaaatg cgtcagccgt    1860
tctgagccca ctggctgaag ccaggcaact ctttcctttc taggaattcc agaggtggct    1920
gctgcttggt gactccctta ttgcaaaccc cggggccaaa aatcccagtc ccactgggtg    1980
cgaggcggag aaatccggcg aggcatttct atggggagcg gccccagca tttaggagtt    2040 agatggtcat cgagacccaa acattagag ccggaaggtg ttaggaagat ataaacgtag    2100
agagcgagta acaggaggca attcacggc caaacaggtt tatttacagg aaagcctgc    2160 gaagagttcc agttaggaat ctggctgaga tcctgatcgc ttacaagctg aggctttat     2220 aataaagttt ctgttgggga ggggttgggg aagtgctggc tagttggaac tgtttggaca    2280 cttttccaact ggggacagat gtggttaggg ccgttaggct ctgttgcggt tagagctgtt    2340
atgctctgtt gaagctatgg acggggttga catttgcttt gtttcttgag aacacagtca    2400
tcaaggttgt aaaatggcat cactattgtt agtcctcaca gaagggactt catacttttt    2460
ctgtctctaa tacttaccta ttcttccccg agtctgtcca cttcctctgg tctctttgac    2520
atcacaaagg agagatggta atggtgggga cgagaataca gagttgtttt tgttgtggtt    2580
ttgttatttt gtgttttaca ctcaaacctc tgtcttctgg aatcccaaag tctagaagaa    2640
gagcgtgtaa acaagtaact gcgtaaaaca gacgtgcatg tgaaatgaag taaaataaaa    2700
taagtgcttg taaatcgatg agaatagcct ctggaacatg ctaagtacgt atgtaggaaa    2760
taaatgtatg tattagtttg aattcgtggc gtggaagaga gaggaaaact aatgggggcaa   2820 aacaagactc agcaggaatc tgccagtgta cactggaaaa ggagcaaagg aaataaattt    2880
ctgggagagg gaatcaaatg tacaaaagca gaactgggt gaaatccttt ggtacatcca     2940
aagaactggg ctgatcagca tgactggaga gtggtatatg tggcagggc accagctctt    3000 actttttttg gatccctaac caaggaattt gagcagtctg atcaaattta catctagaaa    3060
tgttatcttg gcagccatgt ggggatggac tgtaaggaaa tgagactaca ggcagggaga    3120
ccagctagga gactactaca agaatccagg gtagagagag tgagggcctg aatcaaggca    3180
gtagcaatag aaatagagaa gacagataat acatgttaag aggttgaatt gattttttac    3240
aactcattca ttaattatat agattcccat tgaatgcgat cttttgtgcca agggcttgct    3300 ggatataata ataatgaagg acacaaggtc ctcatcctca tggggtttat aatgtaacaa    3360
ggaatacaga cagaaagaga cccagcttat acaattcaag agaccttatt tgagaaaagg    3420
aatacaaaat tacaagtaca acatagata tgaaaatgga gacttaagtc aggtgtaata     3480
gctcacgcct gtaatcccaa cactttgaga ggccgagatg ggaggatctc ttgagtccag    3540
gagttcaaga caagcctggg cgacatagtg agactctgtc tctgcaaaaa ataaaaaata    3600
ttatccaggc acagttactc atgctattag tctcagctac tggggaggct gagcagggat    3660
aatcaccagc tgcagtagcc atgatcgtgc cactgcactc tagcttgagt gacagactga    3720
gaccctgtct ccaaaattaa ataaataaat aaataaagaa ggaaaaagaa aaaaacaaa     3780 aatggagatt tagaatggaa aataggccag gcgtggtggt tcacgcctat aatcctagca    3840
```

```
cattgggagg ctgaggcagg cagattgcat gagctcagga gttcaagacc agcctgggca    3900
acgtggtgaa accccatctc tacccaaaat acaaaaatta gccaggcatt gtggcacatg    3960
cctgtgggtc tgaggtggga ggattgcttg agcctggaag gtggggtttt cagtgagctg    4020
agattgtgcc actgcactcc agcgtggctg acagagtgag atcccatctc gaaaaataaa    4080
taaataaata tagaatggaa aatacattct ttacatcaca t                        4121

<210> SEQ ID NO 3
<211> LENGTH: 118
<212> TYPE: DNA
<213> ORGANISM: Artificial Sequence
<220> FEATURE:
<223> OTHER INFORMATION: bisulfite-treated DNA

<400> SEQUENCE: 3
ttutgggcgu agggaggcgg cgggggguutg utgutgaucg uutcguagcg utggucgggu    60
tucgggagga ggguuucggc gggtggcggc guaggaguuc gagggauag aucgggcg      118

<210> SEQ ID NO 4
<211> LENGTH: 121
<212> TYPE: DNA
<213> ORGANISM: Artificial Sequence
<220> FEATURE:
<223> OTHER INFORMATION: bisulfite-treated DNA

<400> SEQUENCE: 4
agguatttut atgggagcg guuuuagua tttaggagtt agatggtuat cgagauuuaa      60
aauattagag ucggaaggtg ttaggaagat ataaacgtag agagcgagta auaggaggua    120
a                                                                    121

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
ttttgggcgt agggaggc                                                  18

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
cgcccgatct atcccctc                                                  18

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
aggtattttt atggggagc                                                 19

<210> SEQ ID NO 8
```

```
<211> LENGTH: 22
<212> TYPE: DNA
<213> ORGANISM: Artificial Sequence
<220> FEATURE:
<223> OTHER INFORMATION: primer

<400> SEQUENCE: 8
cctcctatta ctcgctctct ac                                              22

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
gggatattaa gtggagttat tttggtttta gtt                                  33

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ccctcccaac atccttccta a                                               21

<210> SEQ ID NO 11
<211> LENGTH: 118
<212> TYPE: DNA
<213> ORGANISM: Homo sapiens

<400> SEQUENCE: 11
ttctgggcgc agggaggcgg cgggggggctg ctgctgaccg cctcgcagcg ctggccgggc     60
tccgggagga gggccccggc gggtggcggc gcaggagccc gagggacag accgggcg        118

<210> SEQ ID NO 12
<211> LENGTH: 121
<212> TYPE: DNA
<213> ORGANISM: Homo sapiens

<400> SEQUENCE: 12
aggcatttct atggggagcg gcccccagca tttaggagtt agatggtcat cgagacccaa     60
aacattagag ccggaaggtg ttaggaagat ataaacgtag agcgagta acaggaggca      120 a                                                                    121
```

DETERMINATION DEVICE, COMPUTER READABLE MEDIUM, AND MARKER FOR OBTAINING INFORMATION ON LUNG CANCER

CROSS REFERENCE TO RELATED APPLICATIONS

This application claims priority from prior Japanese Patent Application No. 2014-142494, filed on Jul. 10, 2014, entitled "METHOD FOR OBTAINING INFORMATION ON LUNG CANCER, AND MARKER AND KIT FOR OBTAINING INFORMATION ON LUNG CANCER", the entire contents of which are incorporated herein by reference.

TECHNICAL FIELD

The present invention relates to a determination device for obtaining information on lung cancer in a subject. Further, the present invention relates to a computer readable medium and a marker for obtaining information on lung cancer.

BACKGROUND

Lung cancer is a malignant tumor that starts in the bronchi or alveoli, and is known as the leading cause of death from malignant tumors. Lung cancer is classified roughly into two types: small-cell lung carcinoma; and non-small-cell lung carcinoma. The non-small-cell lung carcinoma is further classified into three types: adenocarcinoma; squamous-cell carcinoma; and large-cell carcinoma. For screening for lung cancer, chest X-ray and sputum cytology are used. However, it is difficult to find lesions located at sites overlapped with the heart or bones and small lesions by using chest X-ray. The sputum cytology is a test that detects cancer cells in sputum derived from cancerous tissues, but it is difficult to find the cancer cells by only one test and thus multiple tests over several days are necessary. This imposes a large burden on subjects.

For screening for lung cancer, measurement of tumor markers in blood is also performed. The markers for small-cell lung carcinoma to be used are pro-gastrin releasing peptide (ProGRP) and neuron specific enolase (NSE). The markers for lung squamous-cell carcinoma to be used are squamous cell carcinoma antigen (SCC antigen) and cytokeratin 19 fragments (CYFRA). The markers for lung adenocarcinoma to be used are carcinoembryonic antigen (CEA) and sialyl Lewis X-I antigen (SLX). However, these tumor markers have insufficient sensitivity in detecting cancer, and include markers used for cancers of different types from lung cancer.

Meanwhile, new methods for diagnosing cancer based on genetic information have been studied in recent years. The methods include, for example, a method based on information on methylation of DNA. In this method, CpG sites (5'-(CG)-3') in base sequences of certain genes are used as markers. Then, information such as the presence or absence of cancer cells is obtained based on the analysis results of the methylation status of the markers, and is used as an index for diagnosis of cancer.

Methods for determining cancer by DNA methylation analysis have been studied and developed for lung cancer. For example, the publication by Rauch T. et al. discloses that CpG islands of HOXA7 and HOXA9 genes are highly methylated frequently in tissues from stage I lung squamous cell carcinoma (see Rauch T. et al., Proc. Natl. Acad. Sci. USA, vol. 104, p. 5527-5532 (2007)). US 2012/0202202 A discloses a method for detecting various types of cancer including lung cancer by measuring methylation levels in CpG islands of HOXA6, HOXA7, and HOXA9 genes.

Although genes with abnormal methylation in lung cancer have been reported as described above, the number of genes used as markers for detecting lung cancer is few. Thus, there is a demand for development of novel markers for detecting lung cancer using methylation analysis of genes.

SUMMARY OF THE INVENTION

The scope of the present invention is defined solely by the appended claims, and is not affected to any degree by the statements within this summary.

The present inventors have identified novel markers which are genetic regions specifically methylated in DNA obtained from cancerous tissues of lung cancer. The present inventors have found that cancer cells derived from lung cancer can be clearly discriminated from other cells (cells of normal tissues, cells of non-cancerous tissues, and cancer cells derived from cancers of different types from lung cancer) based on the result obtained by analyzing the methylation status of the markers, thereby completing the present invention.

A first aspect of the present invention provides a determination device comprising: a computer system including a computer containing a processor and a memory controlled by the processor, wherein the memory stores a computer program for enabling the computer to carry out a process including the steps of: obtaining an analysis result on methylation status of a CpG site located in a promoter region of at least one gene selected from HOXB4 (Homeobox B4) and ZSCAN31 (zinc finger and SCAN domain containing 31) in a DNA sample derived from a subject; and outputting a determination result as information on lung cancer in the subject based on the resulting analysis result.

A second aspect of the present invention provides a non-transitory computer medium for enabling a computer to provide information on lung cancer in a subject, wherein the medium comprises a computer program for enabling the computer to carry out a process comprising the steps of: obtaining an analysis result on methylation status of a CpG site located in a promoter region of at least one gene selected from HOXB4 and ZSCAN31 in a DNA sample derived from a subject; and providing information on lung cancer in the subject based on the resulting analysis result.

A third aspect of the present invention provides a marker for obtaining information on lung cancer, which is a polynucleotide obtained by subjecting an isolated DNA to bisulfite treatment, wherein the isolated DNA having a contiguous base sequence in an entire or partial promoter region of HOXB4 or ZSCAN31 gene and containing at least one CpG site in the promoter region and at least one cytosine not included in CpG sites.

BRIEF DESCRIPTION OF THE DRAWINGS

FIG. 2A is a graph illustrating a methylation positive rate in a promoter region of HOXB4 gene calculated from methylation data of various clinical specimens;

FIG. 3B is a graph illustrating a methylation positive rate in a promoter region of a known marker gene CDKN2A calculated from methylation data of various clinical specimens;

FIG. 3D is a graph illustrating a methylation positive rate in a promoter region of a known marker gene RUNX3 calculated from methylation data of various clinical specimens;

DETAILED DESCRIPTION OF THE PREFERRED EMBODIMENTS

Figure 1A:
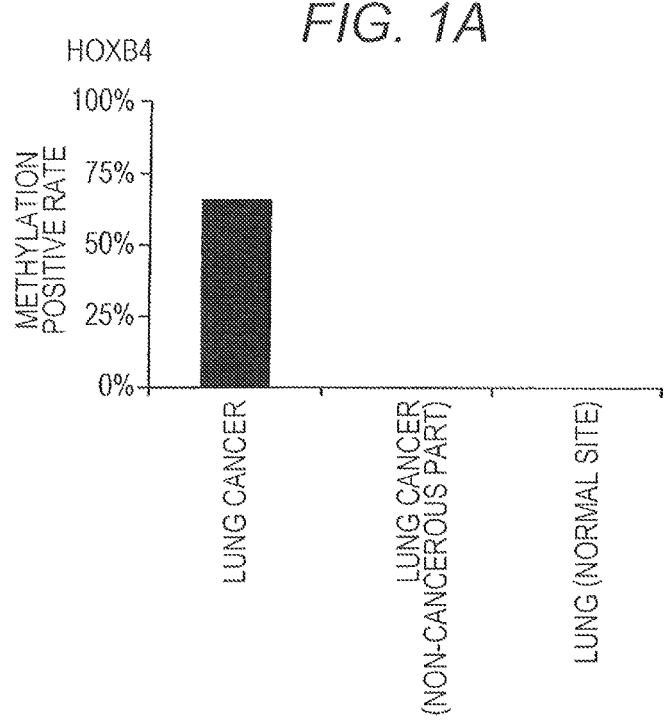
FIG. 1A is a graph illustrating a methylation positive rate in a promoter region of HOXB4 gene calculated from methylation data of cancerous tissues and non-cancerous tissues of lung cancer, and normal lung tissues.
Figure 1B:
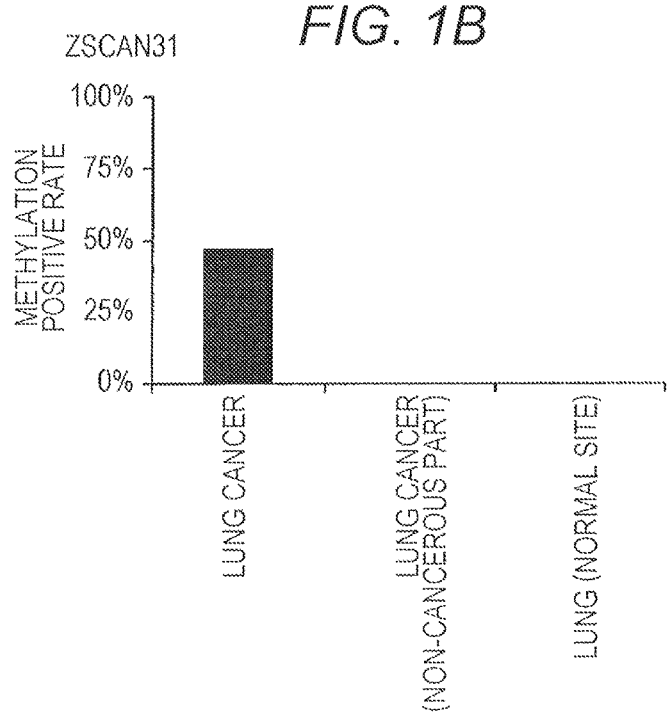
FIG. 1B is a graph illustrating a methylation positive rate in a promoter region of ZSCAN31 gene calculated from methylation data of cancerous tissues and non-cancerous tissues of lung cancer, and normal lung tissues.

In the method for obtaining information on lung cancer of an embodiment (hereinafter also merely referred to as "method"), a DNA sample is first prepared from a biological sample collected from a subject.

In the embodiment, the biological sample is not particularly limited as long as it is a biological sample containing DNA of a subject, but is preferably a sample containing a genomic DNA such as a clinical specimen. Examples of the clinical specimen include body fluid, urine, and tissues obtained by operations or biopsies. Examples of the body fluid include blood, serum, plasma, lymph fluid, ascitic fluid, bone marrow fluid, and nipple discharge. The biological sample may also be a culture obtained by culturing cells or tissues collected from a subject. Further, the biological sample may be a formalin-fixed paraffin-embedded (FFPE) tissue sample collected from a subject.

The DNA sample can be prepared by extracting DNA from the biological sample. A method for extracting DNA from a biological sample is well-known in the art. DNA can be extracted by, for example, mixing the biological sample with a treatment solution containing a surfactant for solubilization of cells or tissues (such as sodium cholate and sodium dodecyl sulfate) and subjecting the resulting mixture to physical procedure (such as stirring, homogenization, and ultrasonication) to release DNA contained in the biological sample into the mixture. In this case, a supernatant containing DNA released by centrifuging the mixture to precipitate cell debris is preferably used in a later-described analyzing step. The obtained supernatant may be purified by any well-known method in the art. DNA can also be extracted from the biological sample and purified by using a commercially-available kit.

Preferably, the above-described preparing step further comprises a step of fragmenting the extracted DNA. By fragmenting the DNA to have appropriate length, methylated DNA immunoprecipitation (MeDIP) and non-methylated cytosine conversion as described below can be effectively performed.

Fragmentation of DNA may be performed by ultrasonication, alkaline treatment, restriction enzyme treatment, or the like. When DNA is fragmented by alkaline treatment, for example, a sodium hydroxide solution is added to a DNA solution to obtain a final concentration of 0.1 to 1.0N and the mixture is incubated at 10 to 40° C. for 5 to 15 minutes to fragment the DNA. When DNA is fragmented by the restriction enzyme treatment, the restriction enzyme is appropriately selected based on the base sequence of DNA, which may be MseI or BamHI, for example.

In the method of the embodiment, the methylation status of a CpG site in a promoter region of at least one gene selected from HOXB4 and ZSCAN31 in the DNA obtained in the preparing step is analyzed.

The term "CpG site" used herein means a site of a sequence in which cytosine (C) and guanine (G) are adjacent in this order from 5' to 3' in the base sequence. The letter "p" in "CpG" represents a phosphodiester bond between cytosine and guanine.

As used herein, "analyzing the methylation status" means analyzing the presence or absence of methylation of a CpG site located in a promoter region of at least one gene selected from HOXB4 and ZSCAN31 or analyzing methylation frequency in the promoter region.

The base sequences of the promoter regions of HOXB4 and ZSCAN31 genes are well-known in the art. These base sequences can be obtained from a well-known database provided by, for example, the National Center for Biotechnology Information (NCBI) (http://www.ncbi.nlm.nih.gov/). The ID numbers of HOXB4 and ZSCAN31 genes are shown in Table 1. The base sequences of the promoter regions of these genes are represented by SEQ ID NOs. 1 and 2, respectively.

TABLE 1

| Gene symbol | Unigene ID | Entrez Gene ID | SEQ ID NO: |
| --- | --- | --- | --- |
| HOXB4 | 2734024 | 3214 | 1 |
| ZSCAN31 | 2725741 | 64288 | 2 |

In the embodiment, the analyzing step may be a step of analyzing the presence or absence of methylation of at least one CpG site among CpG sites located in a promoter region of at least one gene selected from HOXB4 and ZSCAN31. The term "presence or absence of methylation" means whether or not cytosine in a CpG site located in the promoter region is methylated. In the embodiment, only one CpG site may be analyzed, but a plurality of CpG sites is preferably analyzed for the presence or absence of methylation. The CpG sites may be selected in a promoter region of one gene or in each of promoter regions of a plurality of genes.

In another embodiment, the analyzing step may be a step of analyzing methylation frequency in a promoter region of at least one gene selected from HOXB4 and ZSCAN31. The term "methylation frequency" means a ratio of the number of methylated CpG sites relative to the number of CpG sites located in the promoter region. In this embodiment, a target for analysis may be the entire promoter region or a part of the promoter region including at least one CpG site. The target for analysis may contain only one CpG site, but the target for analysis preferably contains a plurality of CpG sites. The target for analysis may be selected in a promoter region of any one of the above genes or in promoter regions of the genes. The positions and number of CpG sites located in the promoter regions of HOXB4 and ZSCAN31 genes are already known, and thus, in the embodiment, the number of methylated CpG sites itself in the promoter regions can be used as the methylation frequency.

The methylation frequency may be a "methylation score" obtained by analyzing methylation status of a CpG site in DNA with mass spectrometry such as MassARRAY® as described below. MassARRAY® allows calculation of a methylation score based on a ratio between the area of a peak derived from methylated DNA fragment and the area of a peak derived from non-methylated DNA fragment obtained through measurement of DNA fragments.

In the embodiment, the methylation frequency in each promotor region of HOXB4 and ZSCAN31 genes may be calculated by a hand method or a machine such as a computer.

In the embodiment, the target for analysis may is not particularly limited, and may be any CpG sites (or certain regions including the CpG sites) in the promoter regions of HOXB4 and ZSCAN31 genes. The target for analysis may be appropriately selected by a person skilled in the art. The positions and number of CpG sites located in the promoter regions of these genes are already known. Thus, the target CpG sites or regions may be selected by routine experiments according to the well-known analysis method described below.

Various methods for analyzing methylation status are well-known in the art. The analysis method to be used in the embodiment is not particularly limited, but preferably includes a step of differentiating methylated DNA from non-methylated DNA, a step of amplifying DNA, and a step of detecting methylated DNA and/or non-methylated DNA.

The step of differentiating methylated DNA from non-methylated DNA may include a step of performing methylation sensitive restriction enzyme treatment, a MeDIP method, non-methylated cytosine converting treatment, or the like.

The step of amplifying DNA may include a step of performing PCR, quantitative PCR, IVT (in vitro transcription) amplification, SPIA (trademark) amplification methods, or the like.

The step of detecting methylated DNA and/or non-methylated DNA may include a step of performing electrophoresis, sequence analysis, microarray analysis, mass spectrometry, Southern hybridization, or the like.

The MeDIP method is used to enrich for methylated DNA in a biological sample by immunoprecipitation using an anti-methylated cytosine antibody or an anti-methylated cytidine antibody, or an antibody which specifically recognizes a methylated DNA-binding protein. In the embodiment, the analyzing step may be a step of enriching for methylated DNA in DNA obtained in the extracting step by the MeDIP method and analyzing methylation status of the obtained methylated DNA. The methylated DNA enriched by the MeDIP method may be amplified by, for example, WT amplification, and the methylation status of the obtained amplified product may be analyzed by using a microarray. This analysis method is referred to as "MeDIP on chip."

The non-methylated cytosine converting treatment is used to react DNA extracted from a biological sample with a non-methylated cytosine conversion agent so as to convert non-methylated cytosine in the DNA to a different base (uracil, thymine, adenine or guanine). The non-methylated cytosine conversion agent is a substance that can react with DNA and convert non-methylated cytosine in the DNA to a different base (uracil, thymine, adenine or guanine). The non-methylated cytosine conversion agent may be, for example, bisulfite such as sodium, potassium, calcium or magnesium bisulfite.

In the treatment using bisulfite, non-methylated cytosine in DNA is converted to uracil due to deamination reaction, while methylated cytosine does not undergo such a base conversion. Thus, the difference in methylation status of a CpG site in DNA is converted to the difference in a base sequence (C and U) by the non-methylated cytosine converting treatment using bisulfite. The non-methylated cytosine converting treatment using bisulfite is referred to as "bisulfite treatment."

When the bisulfite treatment is performed, the additive amount (concentration) of bisulfite is not specifically limited as long as it can sufficiently convert non-methylated cytosine in DNA. For example, the final concentration in a solution containing DNA is 1M or higher, preferably 1M to 15M, and more preferably 3M to 10M. The incubation condition (temperature and time) after addition of bisulfite may be appropriately selected depending on the additive amount of bisulfite. For example, when bisulfite is added at a final concentration of 6M, the incubation is carried out at 50 to 80° C. for 10 to 90 minutes.

Methylation status of CpG sites in DNA can be analyzed by analyzing the sequence of DNA after bisulfite treatment and detecting the difference in base sequence from the original sequence. This method is referred to as "bisulfite sequencing."

The methylation status of CpG sites can be alternatively analyzed by mass spectrometry. Specifically, DNA after bisulfite treatment as a template is amplified by PCR using a primer set specific for a base sequence which is a target for analysis, and the obtained PCR product is subjected to WT amplification to convert methylated cytosine and uracil respectively to guanine (G) and adenine (A). The obtained IVT amplification product is cleaved with RNase A, and the difference in mass (16 Da) due to difference between G and A in the obtained digested fragments is detected using a MALDI-TOF (matrix assisted laser desorption/ionization time-of-flight) mass spectrometer to analyze methylation status of the DNA. This method is referred to as "MassARRAY® analysis."

It is known that the site of IVT product cleaved with RNase A is between an arbitrary base sequence and the adjacent uracil (U) or thymine (T). Thus, the base sequence and mass of the IVT product cleaved with RNase A can be predicted based on the base sequence of the template DNA. Accordingly, it is possible to identify a portion of the base sequence of the template DNA from which each peak obtained in MassARRAY® is originated. For example, when one CpG site is methylated in a DNA fragment, a peak obtained in MassARRAY® shifts to the side with an increased mass for 16 Da. In analysis of a DNA fragment containing plural CpG sites, for example, a shift of 32 Da is shown when two CpG sites are methylated, and a shift of 48 Da is shown when three methylated CpG sites are methylated.

In mass spectrometry such as MassARRAY®, the methylation score of the analyzed DNA fragment can be calculated. For example, when the ratio between the area of the peak of the non-methylated DNA fragment and the area of the peak of the methylated DNA fragment in a chart obtained from the analysis of a DNA fragment having a certain sequence is 1:3, the methylation score of the DNA fragment is 0.75 (=3/(1+3)). The methylation score is theoretically 1 when all CpG sites are methylated, and 0 when not all CpG sites are methylated.

The methylation status of CpG sites can be analyzed by a methylation-specific PCR (MSP) method. The MSP method is a method of analyzing the methylation status of CpG sites (the presence or absence of methylation) by amplifying DNA after bisulfite treatment by PCR using a primer set described below and determining the presence or absence of a PCR product.

The MSP method utilizes a primer set that can amplify a base sequence where a CpG site to be analyzed is methylated (i.e. cytosine is not converted to uracil), but cannot amplify a base sequence where a CpG site is not methylated (i.e. cytosine is converted to uracil). According to the MSP method using such a primer set, the presence of a PCR product indicates the methylation of the CpG site to be analyzed.

The MSP method may also utilize a primer set that cannot amplify a base sequence where cytosine in a CpG site to be analyzed is not converted to uracil, but can amplify a base sequence where cytosine in a CpG site is converted to uracil. In this case, the absence of a PCR product indicates the methylation of the CpG site to be analyzed.

Each primer in the primer set used for the MSP method may be appropriately designed by a person skilled in the art based on the base sequence including a CpG site to be analyzed, and it is preferably designed so as to contain cytosine of the CpG site to be analyzed at the 3' end of the primer or in the vicinity thereof.

The methylation status of CpG sites may alternatively be analyzed with a microarray. In this case, the microarray for analysis may be prepared by immobilizing a nucleic probe complementary to the base sequence of a promoter region of each of HOXB4 and ZSCAN31 genes on a substrate. The microarray can be prepared according to a well-known method in the art.

In the analysis using a microarray, DNA extracted from a biological sample is preferably labeled with a labeling substance well-known in the art. Thus, the determination method of the embodiment preferably further includes a step of labeling the extracted DNA. The labeling step is advantageously carried out after the DNA amplifying step because all DNA in the biological sample can be labeled. Examples of the labeling substance include fluorescent substances, haptens such as biotin, and radioactive substances. Examples of the fluorescent substances include Cy3, Cy5, FITC, and Alexa Fluor™. Labeling of DNA facilitates measurement of a signal from a probe on the microarray. The method for labeling DNA with the labeling substance is well-known in the art.

The above signal may be any suitable signal depending on the type of microarrays. For example, the signal may be an electric signal generated when a DNA fragment hybridizes to a probe on the microarray, or a fluorescence signal or luminescence signal generated from a labeling substance when DNA to be analyzed is labeled as described above. The signal can be detected using a scanner included in a normal microarray analyzer. Examples of the scanner include GeneChip® Scanner3000 7G (Affymetrix, Inc.), and Illumina® BeadArray Reader (Illumina, Inc.).

In the method of the embodiment, information on lung cancer in a subject is obtained based on the analysis result obtained in the analyzing step. In the embodiment, the type of lung cancer is not particularly limited, but is preferably non-small-cell lung carcinoma and more preferably lung squamous cell carcinoma or lung adenocarcinoma. The information on lung cancer is not particularly limited as long as it may be an index on diagnosis of lung cancer or may be used as an auxiliary tool for diagnosis of lung cancer, and is preferably information indicative of occurrence or status of lung cancer or both of them in a subject. The information may include, for example, the presence or absence of cancer cells derived from lung cancer in a biological sample collected from a subject, the possibility of occurrence of lung cancer in a subject, or the risk for future occurrence of lung cancer in a subject. The information on lung cancer in a subject who has already been affected by lung cancer may include prognosis of the subject, or a degree of progression (stage).

In the embodiment, when the analysis result in the analyzing step indicates the presence of methylated CpG sites, information indicating the occurrence of lung cancer or indicating that the status of lung cancer is poor (or aggravated) can be obtained.

In another embodiment, such information can be obtained when the methylation frequency obtained in the analyzing step is higher than or equal to a certain threshold.

More specifically, the information may be indicative of the presence of cancer cells derived from lung cancer in a biological sample. The information may alternatively indicate that a subject has a high risk for being affected by lung cancer or that a subject has already been affected by lung cancer. For a subject who has already been affected by lung cancer, the information may indicate that prognosis of the subject is poor (or aggravated) or that the cancer is in a progressed stage.

In contrast, when the result in the analyzing step indicates the absence of methylated CpG sites, information suggesting no occurrence of lung cancer or information indicating that lung cancer is in a preferable status can be obtained. Alternatively, such information can be obtained when the methylation frequency obtained in the analyzing step is lower than a certain threshold. More specifically, the information may be indicative of the absence of cancer cells derived from lung cancer in a biological sample. The information may alternatively indicate that a subject has a low risk for being affected by lung cancer or that a subject has not been affected by lung cancer. For a subject who has already been affected by lung cancer, the information may be indicative of a preferable prognosis of the subject or indicate that the cancer is in a relatively early stage.

The threshold is not particularly limited and may be empirically set based on accumulated data on various biological samples. The threshold may be alternatively set as follows. First, methylation frequency is analyzed for DNA extracted from a biological sample which is confirmed to be devoid of cancer cells derived from lung cancer (normal lung tissues or normal lung cells) and a biological sample containing a cancer cell derived from lung cancer. Next, based on the obtained analysis results, a threshold is set within a range that is higher than the methylation frequency of the biological sample devoid of cancer cells and lower than the methylation frequency of the biological sample containing the cancer cell. Preferably, the threshold is set as a value that can highly accurately differentiate between the biological sample devoid of cancer cells and the biological sample containing the cancer cell.

The scope of the present invention also encompasses a marker for obtaining information on lung cancer by methylation analysis (also simply referred to as marker"). The marker of the embodiment is at least one CpG site selected from CpG sites located in a promoter region of at least one gene selected from HOXB4 and ZSCAN31 genes. In the embodiment, the methylation status of the marker in a DNA sample prepared from a biological sample collected from a subject may be analyzed, and information on lung cancer in the subject can be obtained based on the analysis result. The analysis of methylation status and the obtainment of information on lung cancer are the same as previously described.

The scope of the present invention encompasses the use of a polynucleotide obtained by subjecting an isolated DNA to bisulfite treatment, in which the isolated DNA has a contiguous base sequence in the entire or partial promoter region of HOXB4 or ZSCAN31 gene and contains at least one CpG site in the promoter region and at least one cytosine not included in CpG sites (also simply referred to as "polynucleotide"), as a marker for obtaining information on lung cancer. The term "cytosine not included in CpG sites" may be any cytosine other than those contained in CpG sites and may include, for example, cytosine in a base sequence in which cytosine (C), and adenine (A), thymine (T) or cytosine (C) are adjacent in this order from 5' to 3' (namely CA, CT or CC).

Regarding the polynucleotide of the embodiment, a nonmethylated cytosine in the isolated DNA is converted to uracil by bisulfate treatment of the isolated DNA, while a methylated cytosine is not converted. In the embodiment, the information on lung cancer can be obtained by analyzing methylation status of CpG sites in the polynucleotide. The isolated DNA can be obtained in the same manner as that described for preparation of the DNA sample. The bisulfite treatment, the analysis of methylation status and the obtainment of information on lung cancer are also the same as previously described.

The size of the polynucleotide of the embodiment is not particularly limited as long as it allows analysis of methylation status by the MSP method, sequencing or mass spectrometry, but is preferably 50 to 200 bases and more preferably 80 to 130 bases. Examples of the polynucleotide of the embodiment include a polynucleotide having base sequences SEQ ID NO: 3 and 4. The polynucleotide having the base sequences SEQ ID NO: 3 and 4 is suitable for analysis of methylation status by the MSP method.

The scope of the present invention encompasses a kit for obtaining information on lung cancer (also simply referred to as "kit"). The kit of the embodiment includes a primer set for analysis of methylation status of at least one CpG site selected from CpG sites located in a promoter region of at least one gene selected from HOXB4 and ZSCAN31 genes.

In the embodiment, the primer set included in the kit may be any primer set for analysis of methylation status of CpG sites according to mass spectrometry such as MassARRAY® or an analysis method involving PCR amplification such as the MSP method and the bisulfite sequencing method, but is preferably a primer set used for mass spectrometry such as Mass ARRAY® or for the MSP. The base sequence of each primer in the primer set may be appropriately selected by a person skilled in the art based on the base sequence in the promoter region. Examples of the primer set include a primer set of primers respectively having base sequences SEQ ID NOs: 5 and 6 and a primer set of primers respectively having base sequences SEQ ID NOs: 7 and 8.

The scope of the present invention also encompasses a system suitable for providing information on lung cancer in a subject. The system may be as follows, for example.

A system suitable for providing information on lung cancer in a subject includes a computer containing a processor and a memory controlled by the processor, wherein the memory stores a computer program for enabling the computer to carry out a process including the steps of:

obtaining an analysis result on methylation status of a CpG site located in a promoter region of at least one gene selected from HOXB4 and ZSCAN31 in a DNA sample derived from a subject; and providing information on lung cancer in the subject based on the resulting analysis result.

The scope of the present invention also encompasses a computer program product for enabling a computer to provide information on lung cancer in a subject. The computer program product may be as follows, for example.

A computer program product for enabling a computer to provide information on lung cancer in a subject includes a computer readable medium, wherein the medium includes a computer program for enabling the computer to carry out a process including the steps of:

obtaining an analysis result on methylation status of a CpG site located in a promoter region of at least one gene selected from HOXB4 and ZSCAN31 in a DNA sample derived from a subject; and providing information on lung cancer in the subject based on the resulting analysis result.

Figure 5:
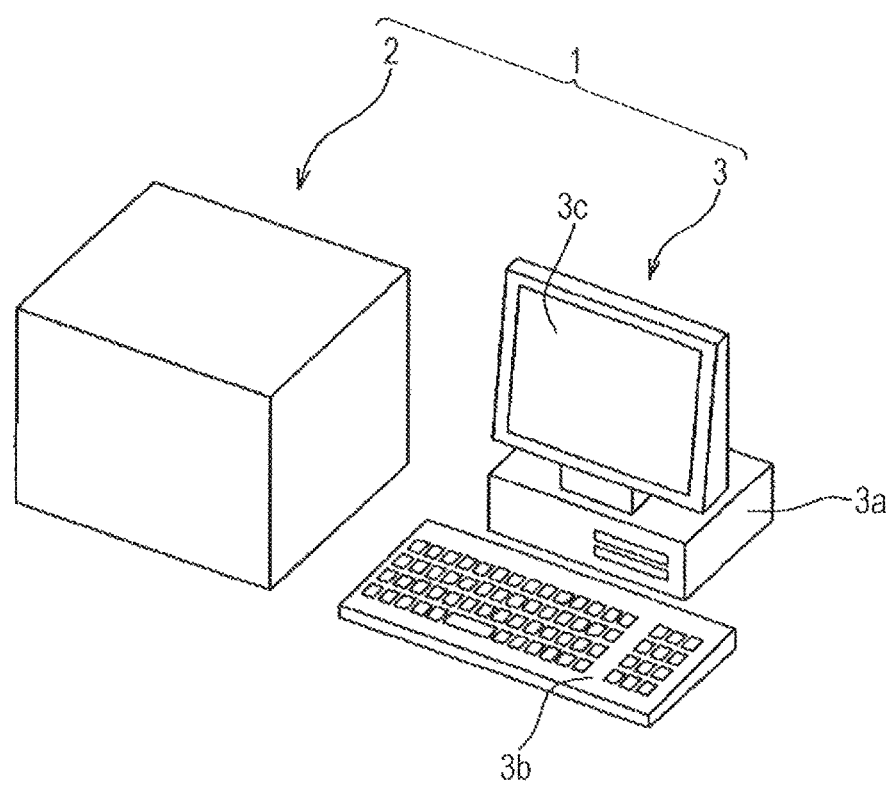
FIG. 5 is a schematic view illustrating one example of a determination device for providing information on lung cancer in a subject.

Hereinafter, an embodiment of a suitable device for carrying out the method of the embodiment will be described with reference to the drawings. However, the present invention is not limited to this embodiment. FIG. 5 is a schematic view of an example of a determination device for providing information on lung cancer in a subject. A determination device 1 illustrated in FIG. 5 includes a measurement device 2 and a computer system 3 connected to the measurement device 2.

In the embodiment, the measurement device 2 is a MALDI-TOF mass spectrometer. The measurement device 2 obtains mass spectrometric information such as the time of flight or the mass-to-charge ratio (m/z value) of a substance to be analyzed. The measurement device 2, onto which a measurement sample prepared from a DNA sample derived from a subject is mounted, obtains mass spectrometric information of a nucleic acid in the measurement sample and sends the mass spectrometric information to the computer system 3.

The measurement device 2 may be, when methylation status is analyzed by the MSP method, a gel imaging device such as a fluorescence image scanner. In this case, the measurement device 2, onto which a gel obtained by electrophoresis of a reaction solution after nucleic acid amplification by the MSP method is mounted, detects amplification products. The measurement device 2 then obtains the band intensity data of the amplification products and sends the obtained data to the computer system 3.

The computer system 3 includes a computer main body 3a, an input device 3b, and a display unit 3c for displaying sample information, determination results and the like. The computer system 3 receives the mass spectrometric information from the measurement device 2. The processor in the computer system 3 executes, based on the mass spectrometric information, a program for providing information on lung cancer in a subject.

Figure 6:
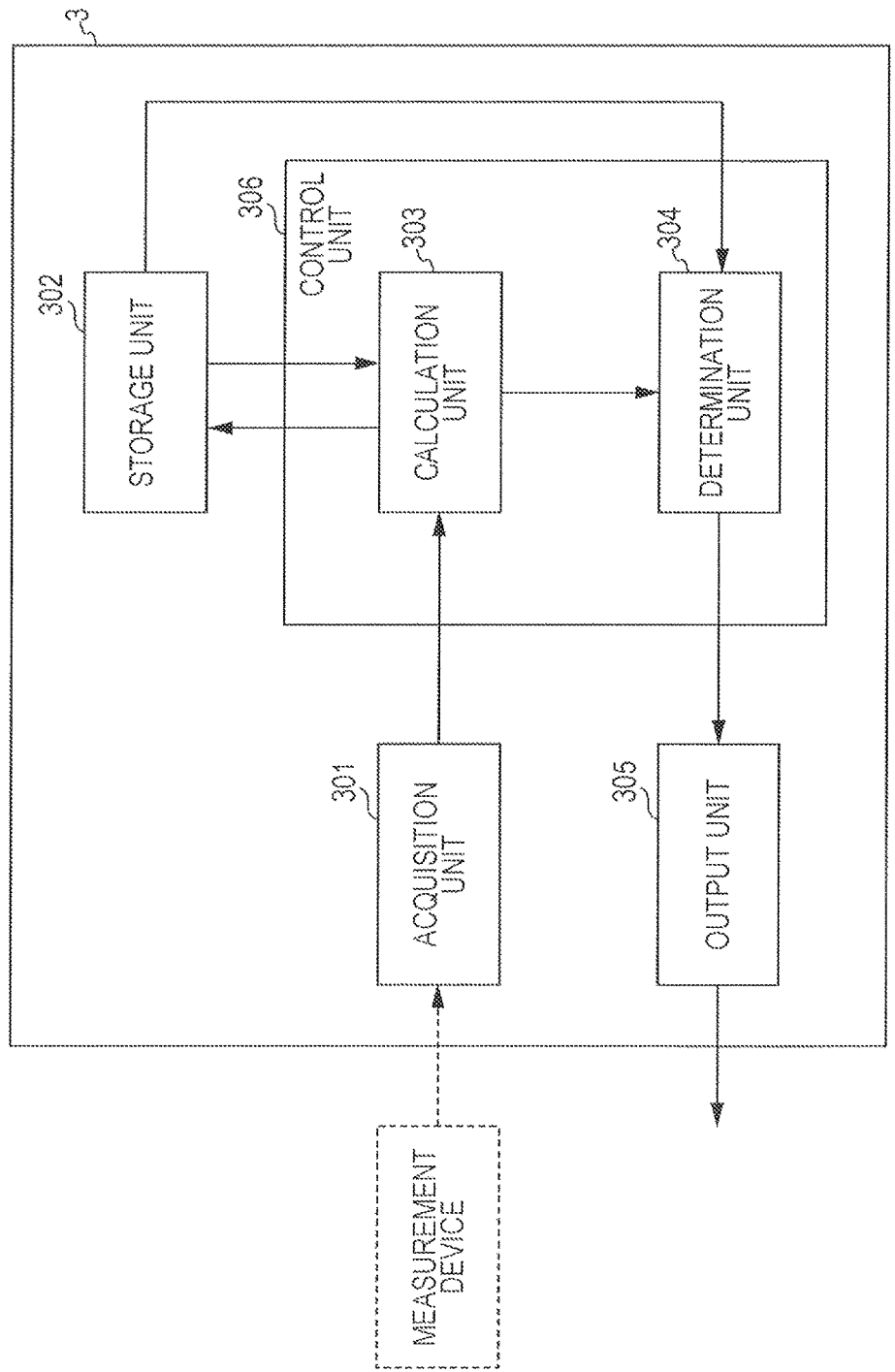
FIG. 6 is a block diagram illustrating the functionality configuration of the determination device of FIG. 5.

FIG. 6 is a block diagram illustrating the functionality configuration of the determination device of FIG. 5. As illustrated in FIG. 6, the computer system 3 includes an acquisition unit 301, a storage unit 302, a calculation unit 303, a determination unit 304, and an output unit 305. The acquisition unit 301 is communicably connected to the measurement device 2 through a network. The calculation unit 303 and the determination unit 304 are included in a control unit 306.

The acquisition unit 301 obtains information from the measurement device 2. The storage unit 302 stores a threshold necessary for determination and a formula for calculating a methylation score. The calculation unit 303 calculates the methylation score from the information obtained at the acquisition unit 301 according to the formula stored in the storage unit 302. The determination unit 304 determines whether or not the methylation score calculated at the calculation unit 303 is lower than the threshold stored at the storage unit 302. The output unit 305 outputs the determination result from the determination unit 304 as information on lung cancer in the subject (e.g., the presence or absence of cancer cells derived from lung cancer in the biological sample collected from the subject).

Figure 7:
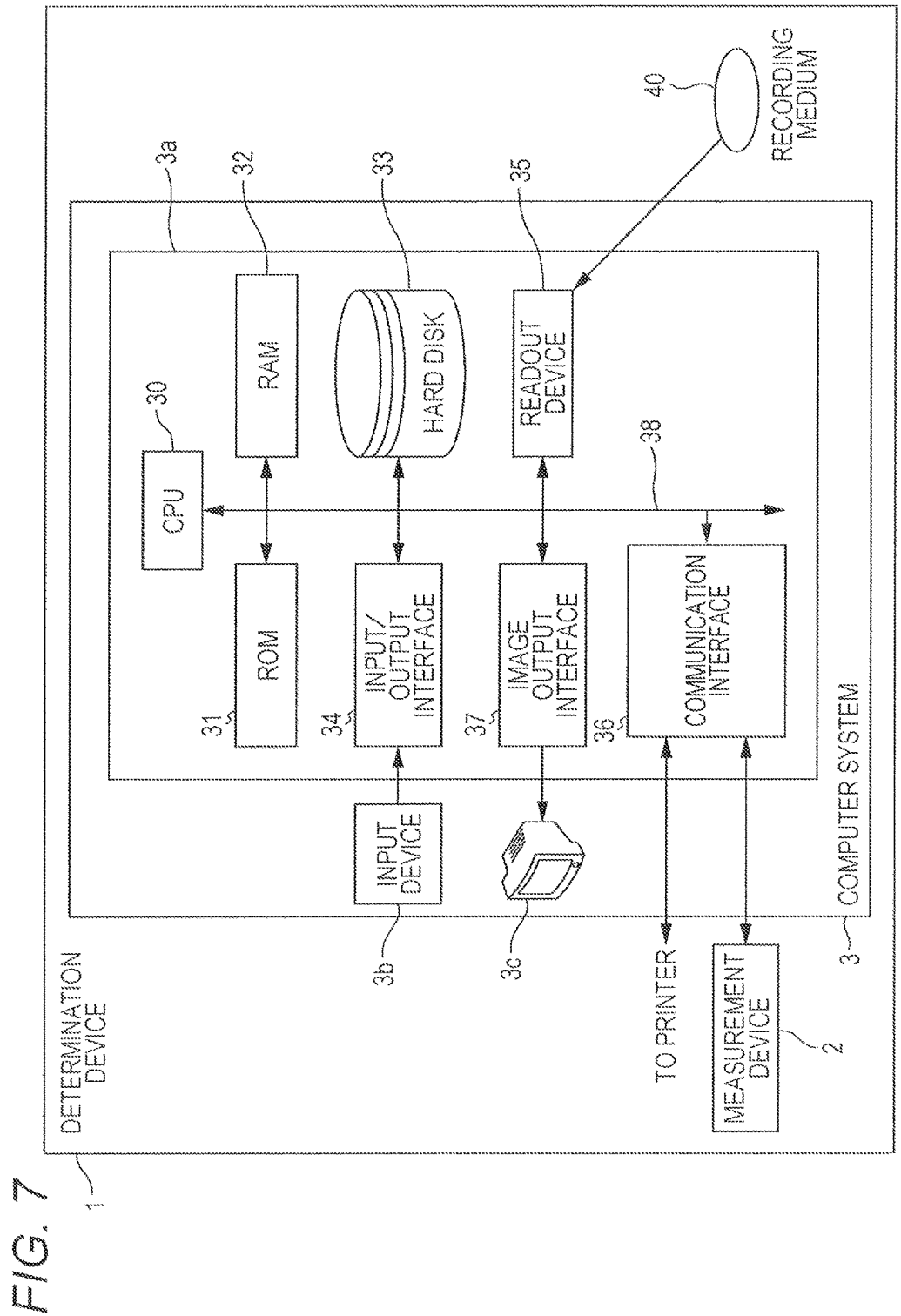
FIG. 7 is a block diagram illustrating the hardware configuration of the determination device illustrated in FIG. 5.

FIG. 7 is a block diagram illustrating the hardware configuration of the determination device in FIG. 5. As illustrated in FIG. 7, the computer main body 3a includes a central processing unit (CPU) 30, a read only memory (ROM) 31, a RAM 32, a hard disk 33, an input/output interface 34, a readout device 35, a communication interface 36, and an image output interface 37. The CPU 30, ROM 31, a random access memory (RAM) 32, the hard disk 33, the input/output interface 34, the readout device 35, the communication interface 36, and the image output interface 37 are data-communicably connected via a bus 38.

The CPU 30 can execute a computer program stored in the ROM 31 and a computer program loaded with the RAM 32. When the CPU 30 executes the application program, the functional blocks described above may be executed. Accordingly, the computer system serves as a terminal that is a determination device for providing information on lung cancer in a subject.

ROM 31 is configured to include mask ROM, PROM, EPROM, EEPROM, and the like. ROM 31 stores the computer program executed by the CPU 30 and data used for the execution.

ROM 32 is configured to include SRAM, DRAM, and the like. ROM 32 is used for readout of the computer programs stored in ROM 31 and the hard disk 33. ROM 32 is also used as a work area of CPU 30 in executing these computer programs.

The computer programs, such as an operating system and an application program (a computer program for providing information on lung cancer in a subject), to be executed by the CPU 30, and data for executing the computer programs are installed on the hard disk 33.

The readout device 35 is configured to include a flexible disk drive, a CD-ROM drive, a DVD-ROM drive, and the like. The readout device 35 can read out the computer program or data stored on a portable recording medium 40.

The input/output interface 34 is configured to include a serial interface such as USB, IEEE1394, and RS-232C, a parallel interface such as SCSI, IDE, and IEEE1284, an analog interface formed by a D/A converter and an A/D converter, and the like. The input/output interface 34 is connected to the input device 3b such as a keyboard and a mouse. A user can input the data into the computer main body 3a by means of the input device 3b.

The communication interface 36 is, for example, an Ethernet® interface. The computer system 3 can send printing data to a printer via the communication interface 36.

The image output interface 37 is connected to the display unit 3c including a LCD, a CRT and the like. Accordingly, the display unit 3c can output an image signal according to image data from the CPU 30. The display unit 3c displays an image (on a screen) according to the input image signal.

Figure 8:
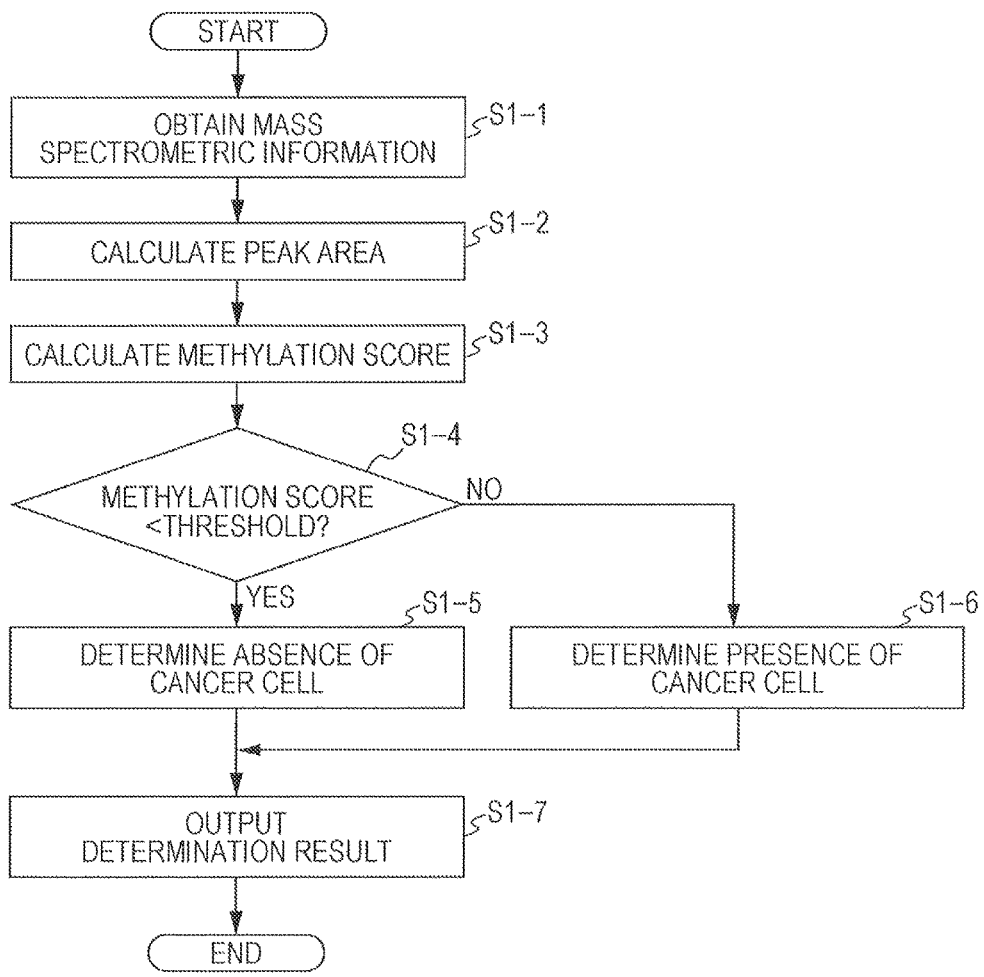
FIG. 8 is a flow chart of determination for providing information on lung cancer in a subject using the determination device illustrated in FIG. 5.

Subsequently, the processing procedure performed by the determination device 1 for providing information on lung cancer in a subject will be described. FIG. 8 is a flow chart for providing information on lung cancer using the determination device of FIG. 5. An illustrated example, a peak area is calculated based on mass spectrometric information of a nucleic acid in a measurement sample prepared from a DNA sample derived from a subject, and a methylation score is calculated from the obtained peak area, so as to determine whether or not the methylation score is lower than a threshold. However, the present invention is not limited to this embodiment.

In the step S1-1, the acquisition unit 301 in the determination device 1 obtains mass spectrometric information from the measurement device 2. In the step S1-2, the calculation unit 303 calculates a peak area from the mass spectrometric information obtained at the acquisition unit 301 and sends the peak area to the storage unit 302. In the step S1-3, the calculation unit 303 calculates a methylation score based on the peak area stored in the storage unit 302 according to the formula stored in the storage unit 302.

In the step S1-4, the determination unit 304 determines whether or not the methylation score calculated at the calculation unit 303 is lower than the threshold stored in the storage unit 302. When the methylation score is lower than the threshold, the process proceeds to the step S1-5 and the determination unit 304 sends, to the output unit 305, a determination result indicating that the biological sample collected from the subject does not contain cancer cells derived from lung cancer. When the methylation score is not lower than the threshold (i.e., the methylation score is the threshold or more), the determination unit 304 sends, to the output unit 305, a determination result indicating that the biological sample collected from the subject contains cancer cells derived from lung cancer (see step S1-6).

In the step S1-7, the output unit 305 outputs the determination result as information on lung cancer in the subject, so that the display unit 3c displays the result and/or the printer prints out the result. Accordingly, the determination device can provide, to a physician or the like, information assisting the physician or the like to judge whether or not the subject has lung cancer.

Hereinafter, the present invention will be described in detail with reference to Examples, but the present invention is not limited thereto.

EXAMPLES

Example 1: Identification of Novel Markers Utilizing Methylation Data of Cancerous Tissues and Non-Cancerous Tissues of Lung Cancer and Normal Lung Tissues (1) Collection of Methylation Data In Example 1, Methylation data on Infinium HumanMethylation450 BeadChip (Illumina, Inc.), which are published in TCGA (The Cancer Genome Atlas: tcga-data.nci.nih.gov/tcga/tcgaHome2.jsp), were collected for cancerous tissues (370 specimens) and non-cancerous tissues (75 specimens) of lung cancer. The cancerous tissue specimens include 220 adenocarcinoma specimens and 150 squamous cell carcinoma specimens. Further, methylation data on Infinium HumanMethylation450 BeadChip, which are published in the publication of Nazor K L et al. (Recurrent variations in DNA methylation in human pluripotent stem cells and their differentiated derivatives. Cell Stem Cell 2012; 10(5): 620-634), were collected for normal lung tissues (2 specimens).

(2) Identification of Novel Markers

As a result of data mining using Infinium HumanMethylation 450BeadChip (Illumina, Inc.), the promotor regions of HOXB4 and ZSCAN31 genes were identified as markers which are specifically methylated in cancerous tissues of lung cancer (see FIGS. 1A and B). These markers are also referred to as the present markers hereinbelow.

Example 2: Comparison of Methylation Data Between Cancer/Tumor Tissue Specimens Derived from Plural Types of Cancer/Tumor, Non-Cancerous Tissue Specimens, and Normal Tissue Specimens (1) Collection of Methylation Data In Example 2, methylation data of 11 types of cancer/tumor tissue specimens, 9 types of non-cancerous tissue specimens, and 19 types of normal tissue specimens were compared. The number of specimens for the respective tissues is shown in the following tables.

TABLE 2

Cancer/tumor tissue

| Tissue | The number of specimens |
| --- | --- |
| Brain tumor (Brain) | 114 |
| Head and neck cancer (Head and neck) | 293 |
| Thyroid cancer (Thyroid) | 230 |
| Breast cancer (Breast) | 548 |
| Lung cancer (Lung) | 370 |
| Liver cancer (Liver) | 99 |
| Colon cancer (Colon) | 324 |
| Uterine body cancer (Uterus) | 334 |
| Renal cancer (Kidney) | 282 |
| Leukemia (AML) | 192 |
| Malignant melanoma (Melanoma) | 242 |

TABLE 3

Non-cancerous tissue

| Tissue | The number of specimens |
| --- | --- |
| Brain tumor (Brain) | 2 |
| Head and neck cancer (Head and neck) | 50 |
| Thyroid cancer (Thyroid) | 28 |
| Breast cancer (Breast) | 98 |
| Lung cancer (Lung) | 75 |
| Liver cancer (Liver) | 19 |
| Colon cancer (Colon) | 40 |
| Uterine body cancer (Uterus) | 36 |
| Renal cancer (Kidney) | 164 |

TABLE 4

Normal tissue

| Tissue | RCAST | Literature 1 | Literature 2 | Total |
| --- | --- | --- | --- | --- |
| Normal brain (Brain) | 2 | 1 | 0 | 3 |
| Normal oral cavity (Oral) | 2 | 0 | 0 | 2 |
| Normal lung (Lung) | 0 | 2 | 0 | 2 |
| Normal colonic mucosa (Colon) | 2 | 0 | 0 | 2 |
| Normal liver (Liver) | 2 | 0 | 0 | 2 |
| Peripheral blood from healthy subjects (Blood) | 2 | 2 | 0 | 4 |
| Normal skeletal muscle (Skeletal) | 2 | 2 | 0 | 4 |
| Normal testis (Testis) | 1 | 0 | 0 | 1 |
| Normal gastric mucosa (Stomach) | 0 | 1 | 0 | 1 |
| Normal pancreas (Pancreas) | 0 | 2 | 0 | 2 |
| Normal spleen (Spleen) | 0 | 2 | 0 | 2 |
| Normal kidney (Kidney) | 0 | 0 | 0 | 0 |
| Normal adrenal gland (Adrenal gland) | 0 | 2 | 0 | 2 |
| Normal ureter (Ureter) | 0 | 2 | 0 | 2 |
| Normal bladder (Bladder) | 0 | 2 | 0 | 2 |
| Normal lymph nodes (Lymph nodes) | 0 | 2 | 0 | 2 |
| Normal adipose tissue (Adipose tissue) | 0 | 2 | 0 | 2 |
| Normal heart (Heart) | 0 | 1 | 0 | 1 |
| Various normal blood cell components (WB, PBMC, Gran, CD4$^+$, CD8$^+$, CD14$^+$, CD19$^+$, CD56$^+$, Neu, Eos) | 0 | 0 | 60 | 60 |

In Table 4, the methylation data for the specimens indicated in the column "RCAST" were obtained by the present inventors according to Infinium Methylation Assay using Infinium HumanMethylation450 BeadChip (Illumina, Inc.). The methylation data for the specimens indicated in the columns "Literature 1" and "Literature 2" were methylation data published in the following literatures obtained with Infinium HumanMethylation450 BeadChip (Illumina, Inc.).

Literature 1: Nazor K L et al., Recurrent variations in DNA methylation in human pluripotent stem cells and their differentiated derivatives. Cell Stem Cell 2012; 10(5): 620-634

Literature 2: Reinius L E et al., Differential DNA Methylation in Purified Human Blood Cells: Implications for Cell Lineage and Studies on Disease Susceptibility, PLoS One, 7(7) e41361

The methylation data in this context are the methylation rate (mCpG) of CpG sites in HOXB4 and ZSCAN31 obtained as follows. The Infinium HumanMethylation450 BeadChip include probes for methylated CpG sites and probes for non-methylated CpG sites of 482,421 CpG sites on human genome. The signal intensity (signal M) from the probes for methylated CpG sites and the signal intensity (signal U) from the probes for non-methylated CpG sites in the target genes were detected on Bead Array Reader, and the methylation rate (mCpG) of CpG sites in the respective genes was calculated according to the following calculation formula:

$$(mCpG) = (\text{signal } M) / \{(\text{signal } M) + (\text{signal } U)\}$$

(2) Comparison of Methylation Positive Rates Between Cancer/Tumor Tissue Specimens, Non-Cancerous Tissue Specimens, and Normal Tissue Specimens The obtained methylation rate (mCpG) was defined as "methylation positive" when a statistically significant difference between tumor tissue specimens and normal tissue specimens was observed. Then, the methylation positive rate (%) for each cancer was calculated according to the following formula:

Methylation positive rate (%)=(the number of methylation positive specimens/the total number of specimens)×100

For example, for brain tumor, the methylation positive rate was calculated by "(the number of methylation positive specimens among the brain tumor tissue specimens/the total number of the brain tumor tissue specimens=114)×100."

Figure 2B:
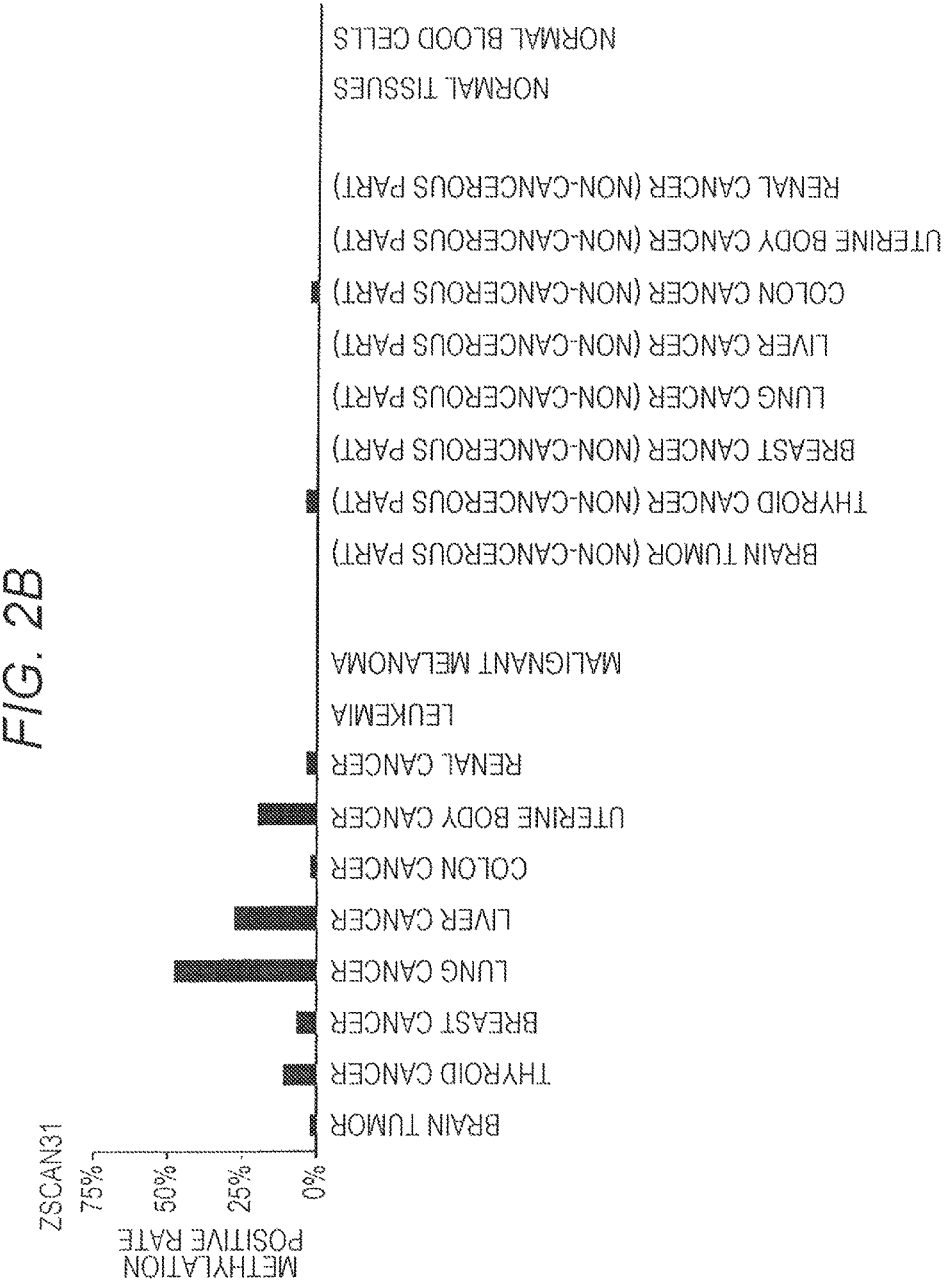
FIG. 2B is a graph illustrating a methylation positive rate in a promoter region of ZSCAN31 gene calculated from methylation data of various clinical specimens.

The results are shown in FIGS. 2A and 2B. In FIG. 2, "normal tissues" represent, among the tissues indicated in Table 4, normal tissues excluding 60 specimens of various normal blood cell components, and "normal blood cells" represent the 60 specimens of various normal blood cell components. As obvious from FIGS. 2A and 2B, all the present markers were rarely methylated in non-cancerous tissues, human normal tissues, and human normal blood cells. Further, all the present markers are specifically highly methylated in lung cancer, compared to other types of cancer. Therefore, the present markers are suitable for detection of lung cancer.

Comparative Example 1: Comparison of Methylation Positive Rates Among Cancer/Tumor Tissue Specimens Derived from Plural Types of Cancer/Tumor, Non-Cancerous Tissue Specimens, and Normal Tissue Specimens The methylation positive rate was calculated for HOXA7, CDKN2A, DAPK1, and RUNX3 genes (hereinafter referred to as "known markers") which have already been known to be methylated in cancer cells derived from lung cancer in the similar manner as Example 2 in the respective tissues. The results are shown in FIGS. 3A, 3B, 3C, and 3D.

Figure 3A:
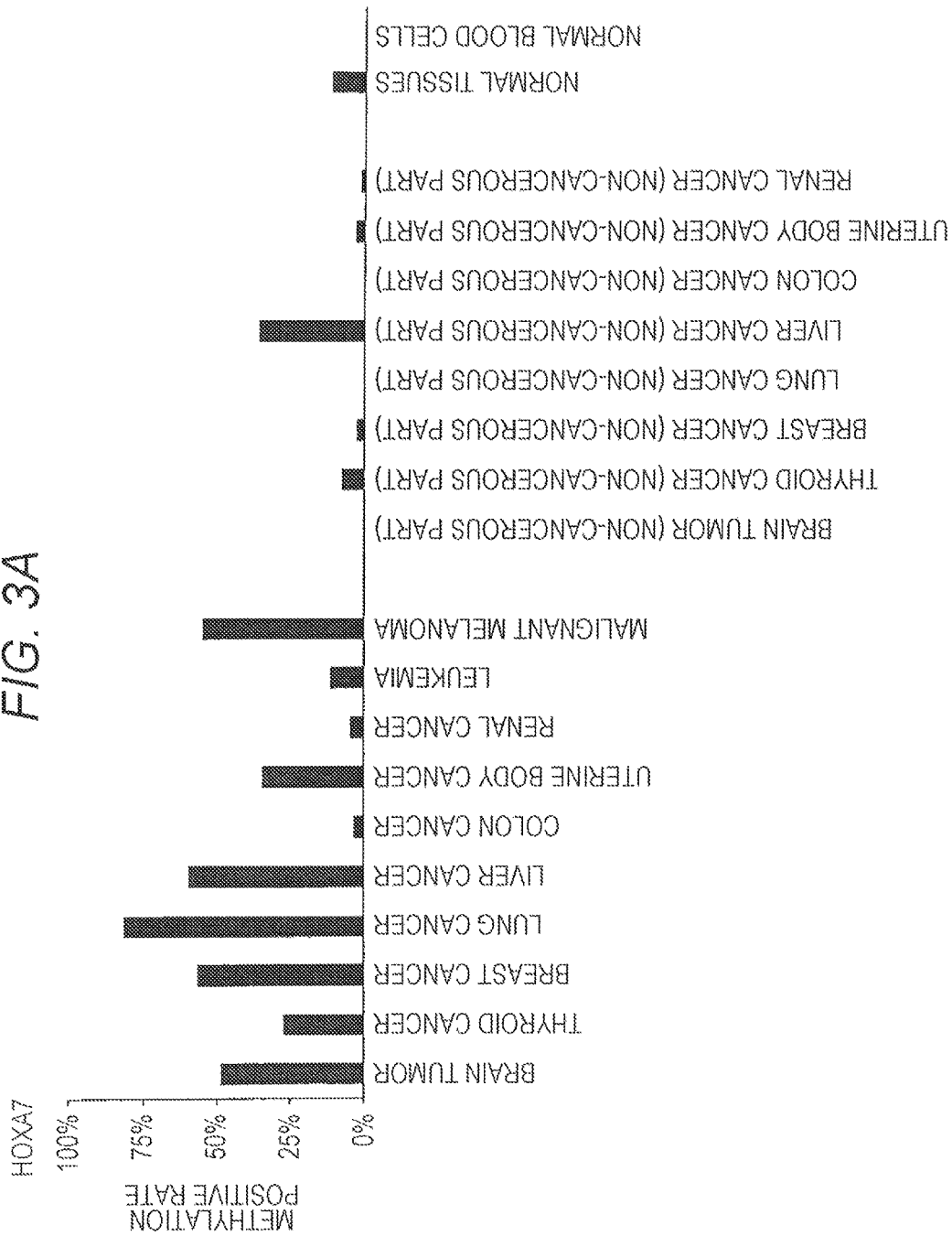
FIG. 3A is a graph illustrating a methylation positive rate in a promoter region of a known marker gene HOXA7 calculated from methylation data of various clinical specimens.
Figure 3C:
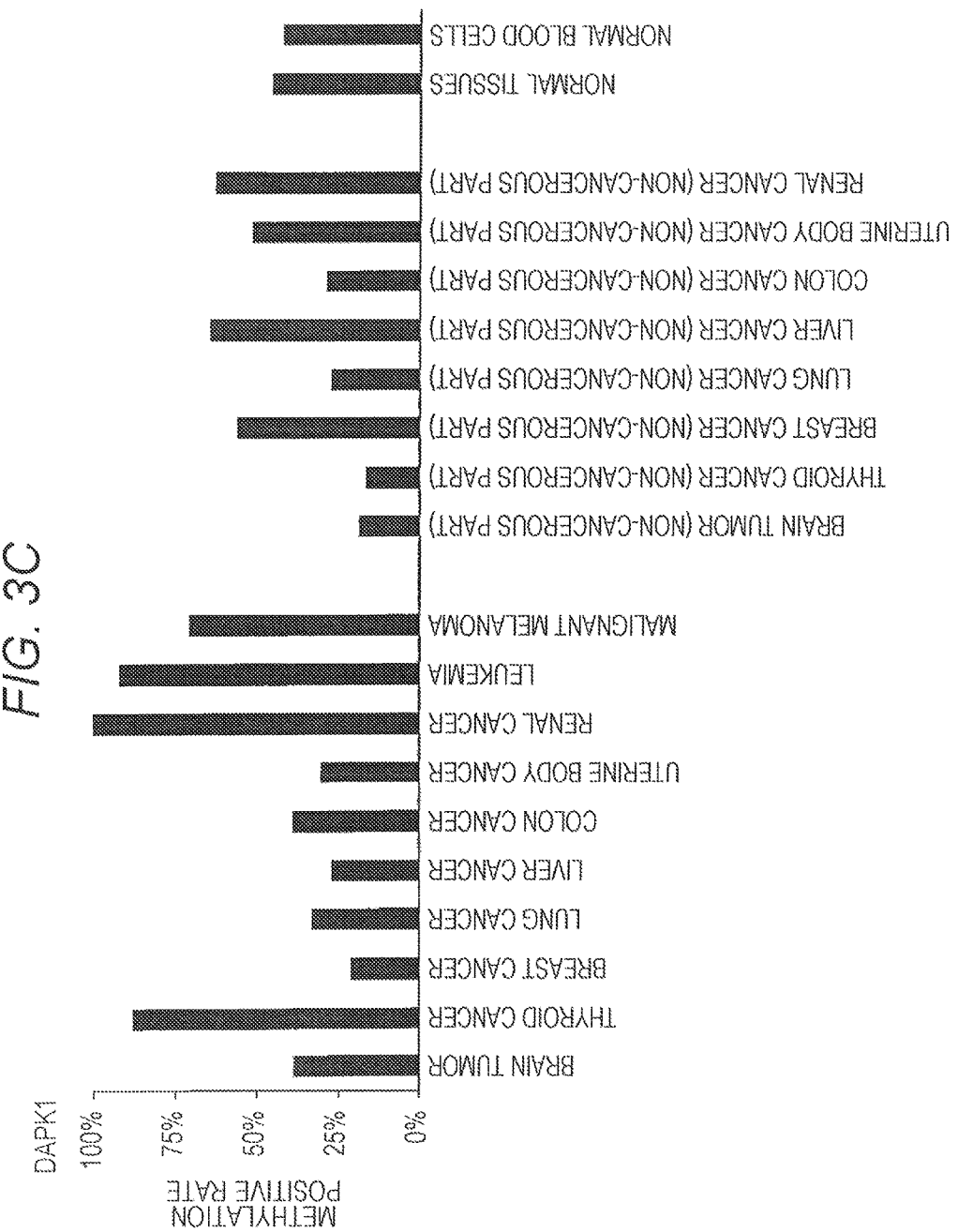
FIG. 3C is a graph illustrating a methylation positive rate in a promoter region of a known marker gene DAPK1 calculated from methylation data of various clinical specimens.

As obvious from FIG. 3A, in HOXA7, the positive rate in lung cancer was high, but the methylation was also detected in other types of cancer. Thus, HOXA7 has low specificity to lung cancer. As obvious from FIGS. 3B, 3C, and 3D, in CDKN2A, DAPK1, and RUNX3 genes, the positive rates in lung cancer were high, but the methylation was also detected in other types of cancer, normal tissues, and normal blood cells. Thus, CDKN2A, DAPK1, and RUNX3 genes have low specificity to lung cancer. Therefore, the sensitivity of the known markers for lung cancer is high, but their specificity to lung cancer is low. Accordingly, these known markers have issues in terms of performance as diagnostic markers of lung cancer. It turns out, from comparison of Comparative Example 1 to Example 2, that the present markers are more useful in detecting lung cancer, compared to the known markers.

Example 3: Comparison of Methylation Data (MSP) Between Tissues from Healthy Subjects and Tissues from Lung Cancer Patients (1) Biological Samples In Example 3, as biological samples, FFPE cancerous tissues collected from lung adenocarcinoma patients (6 specimens) and FFPE cancerous tissues collected from lung squamous cell carcinoma patients (5 specimens) were used. As control samples, normal lung tissues (2 specimens) were used.

(2) Preparation of Measurement Samples (i) Extraction of Genomic DNA

Genomic DNA was extracted from the above FFPE lung cancer tissues with the use of QIAamp DNA FFPE Tissue Kit (QIAGEN). Genomic DNA was extracted from normal tissues with the use of QIAamp DNA Mini Kit (QIAGEN). Genomic DNA of human peripheral blood lymphocytes was used as the control genomic DNA. The genomic DNA from human peripheral blood lymphocytes was amplified with the use of GenomiPhi v2DNA Amplification Kit (GE Healthcare Life Sciences). The obtained amplified product consisted of non-methylated DNA. The amplification product was fragmented with Bioruptor (COSMO BIO Co., Ltd.) to obtain a solution of non-methylated DNA fragments (0% methylated DNA). A portion of the solution of non-methylated DNA fragments was subjected to reaction with SssI methylase (New England Biolabs) to methylate all cytosines in CG sequences, and a solution of methylated DNA fragments (100% methylated DNA) was obtained.

(ii) Bisulfite Treatment

The respective DNA fragments (500 ng) obtained as described above were subjected to bisulfite treatment with the use of EZ DNA Methylation Kit (Zymo Research), and the treated genomic DNA was dissolved in sterilized distilled water (80 µl).

(3) MSP

MSP was carried out using the measurement samples and control samples obtained in the above section (2). The composition of the PCR reagent, primer sets, and reaction conditions for PCR are shown below.

| <PCR Reagent> | |
|---|---|
| DW (sterilized water) | 16.8 µL |
| 10 × PCR buffer with MgCl2 (Roche) | 2.5 µL |
| 2 mM dNTP mix | 2.5 µL |
| 10 µM sense primer | 1.0 µL |
| 10 µM antisense primer | 1.0 µL |
| Faststart Taq polymerase (Roche) | 0.2 µL |
| Measurement sample | 1.0 µL |
| Total | 25.0 µL |

<Primer Set>

The primer sets used for MSP are shown in Table 5. These primer sets allow generation of amplification products when DNA in the target regions is methylated (hereinafter also referred to as "primer set for methylation detection"). As a primer set for accuracy control, a primer set that allows judgment on whether or not the bisulfite treatment has been appropriately performed (see Table 6). The base sequences of regions which are analyzed with the primer sets for methylation detection in the promoter regions of HOXB4 and ZSCAN31 genes are shown in SEQ ID NOs: 11 and 12, respectively.

TABLE 5

| Gene name | Primer | Base sequence | SEQ ID NO: | PCR product (bp) | Annealing temp. (X) | Cycles (Y) | Amplified gene region |
|---|---|---|---|---|---|---|---|
| HOXB4 | HOXB4_MSP_top_MF | TTTTGGGCGTAGSGAGGC | 5 | 118 | 68 | 36 | chr17: 46, 655, 308-46, 655,425 |
|  | HOXB4_MSP_top_MR | CGCCCGATCTATCCCCTC | 6 |  |  |  |  |
| ZSCAN31 | ZSCAN31_MSP_top_MF | AGGTATTTTTATGGGGAGC | 7 | 118 | 60 | 36 | chr6: 28, 304, 090-28, 304,210 |
|  | ZSCAN31_MSP_top_MR | CCTCCTATTACTCGCTCTCTAC | 8 |  |  |  |  |

TABLE 6

| Primer for accuracy control | Base sequence | SEQ ID NO: | PCR product (bp) | Annealing temp. (X) | Cycles (Y) |
|---|---|---|---|---|---|
| Forward | GGGATATTAAGTGGAGTTATTTTSGTTTTAGTT | 9 | 129 | 60 | 40 |
| Reverse | CCCTCCAACATCCTTCCTAA | 10 | | | |

<PCR Reaction Conditions>
95° C. for 6 minutes;
Y cycles of 95° C. for 30 seconds, X° C. for 30 seconds, and 72° C. for 30 seconds;
72° C. for 7 minutes; and
keep at 16° C.

In the above reaction conditions, "X" and "Y" respectively represent the annealing temperature and the number of cycles as indicated in Tables 5 and 6.

(4) Analysis of Results of Methylation-Specific PCR (MSP)

Figure 4:
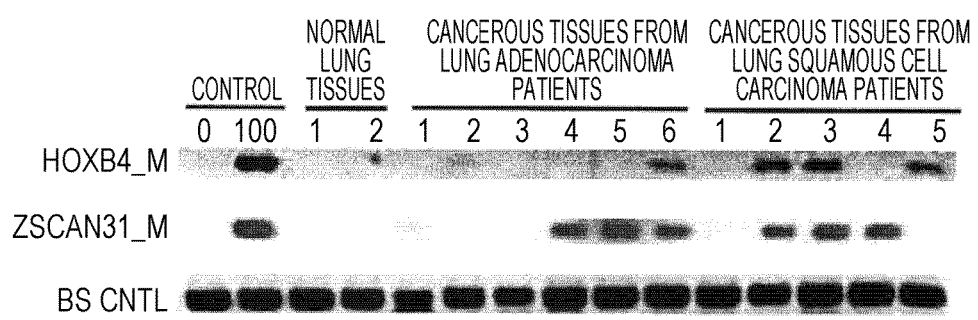
FIG. 4 is an image describing the results of methylation-specific PCR (MSP) amplification of DNA extracted from normal lung tissues and cancerous tissues derived from a lung cancer patient using the respective primer sets for HOXB4 and ZSCAN3.

The amplified product obtained from MSP was verified by 2% agarose gel electrophoresis. The results are shown in FIG. 4. In this figure, "0" and "100" under "control" represent the 0% methylation control sample and the 100% methylation control sample, respectively.

In PCR using the primer set for accuracy control, bands were detected for all the samples as shown in FIG. 4. This shows that bisulfite treatment of the samples was appropriately carried out. In PCR using the primer sets for methylation detection, bands derived from methylated CpGs were not detected for any normal lung tissues. In contrast, in PCR for lung cancer tissue samples, bands were detected in 4 samples among 11 samples for HOXB4 and in 6 samples among 11 samples for ZSCAN31. Accordingly, it turns out that in methylation analysis of the present markers by the MSP method, the methylation of the present markers and lung cancer were correlated similarly to the result from Infinium method of Example 1. Specifically, it turns out that HOXB4 and ZSCAN31 are highly specific markers which are highly methylated in lung cancer, but methylation of which is not detected in normal lung tissues.

What is claimed is:

1. A determination device comprising:
  a measurement device operable to perform a physical assay step on a DNA sample derived from a subject using as a marker a polynucleotide having a base sequence SEQ ID NO: 3 or 4; and
  a computer system, connected to the measurement device, including a computer containing a processor and a memory controlled by the processor, wherein
    the memory stores a computer program for enabling the computer to carry out a process including the steps of:
      obtaining, based on a result of the physical assay step performed by the measurement device, an analysis result on methylation status of at least one CpG site located in a promoter region of at least one gene selected from HOXB4 and ZSCAN31 in the DNA sample; and
      outputting a determination result as information on lung cancer in the subject based on the analysis result.

2. The determination device according to claim 1, wherein the analysis result is presence or absence of methylation of the at least one CpG site.

3. The determination device according to claim 2, wherein the information on lung cancer in the subject is presence or absence of a cancer cell derived from lung cancer in the biological sample collected from the subject, and the step of outputting information is the step of outputting information indicating that the biological sample contains a cancer cell derived from lung cancer when the analysis result indicates the presence of a methylated CpG site.

4. The determination device according to claim 1, wherein the analysis result is methylation frequency.

5. The determination device according to claim 4, wherein the information on lung cancer in the subject is presence or absence of a cancer cell derived from lung cancer in the biological sample collected from the subject, and the step of outputting information is the step of outputting information indicating that the biological sample contains a cancer cell derived from lung cancer when the methylation frequency is higher than a predetermined threshold.

6. The determination device according to claim 1, wherein the analysis result is obtained by using a kit for obtaining information on lung cancer, comprising a primer set for analyzing the methylation status of the at least one CpG site selected from CpG sites located in a promoter region of at least one gene selected from HOXB4 and ZSCAN31.

7. The determination device according to claim 6, wherein the primer set is a primer set for analyzing the methylation status of the at least one CpG site by at least one method selected from mass spectrometry and methylation-specific PCR method.

8. The determination device according to claim 7, wherein the primer set is at least one selected from a primer set of primers respectively having base sequences SEQ ID NOs: 5 and 6 and a primer set of primers respectively having base sequences SEQ ID NOs: 7 and 8.

9. The determination device according to claim 1, wherein the measurement device is a mass spectrometer.

10. The determination device according to claim 1, wherein the measurement device is a fluorescence image scanner.

* * * * *